United States Patent
Cabiri et al.

(10) Patent No.: US 9,393,369 B2
(45) Date of Patent: Jul. 19, 2016

(54) STABILIZED PEN INJECTOR

(71) Applicant: MEDIMOP Medical Projects Ltd., Ra'anana (IL)

(72) Inventors: Oz Cabiri, Macabim-Reut (IL); Ran Hezkiahu, Herzliya (IL)

(73) Assignee: MEDIMOP MEDICAL PROJECTS LTD., Ra'anana (IL)

( * ) Notice: Subject to any disclaimer, the term of this patent is extended or adjusted under 35 U.S.C. 154(b) by 45 days.

(21) Appl. No.: 14/096,977

(22) Filed: Dec. 4, 2013

(65) Prior Publication Data

US 2014/0163526 A1  Jun. 12, 2014

Related U.S. Application Data

(63) Continuation-in-part of application No. 13/063,236, filed as application No. PCT/US2009/056778 on Sep. 14, 2009, now Pat. No. 8,617,126.

(60) Provisional application No. 61/884,597, filed on Sep. 30, 2013, provisional application No. 61/192,198, filed on Sep. 15, 2008.

(51) Int. Cl.
  *A61M 5/32* (2006.01)
  *A61M 5/20* (2006.01)
  *A61M 5/42* (2006.01)

(52) U.S. Cl.
  CPC .............. *A61M 5/3287* (2013.01); *A61M 5/20* (2013.01); *A61M 5/425* (2013.01); *A61M 5/3204* (2013.01); *A61M 5/326* (2013.01);

(Continued)

(58) Field of Classification Search
  CPC ... A61M 2207/00; A61M 5/20; A61M 5/326; A61M 5/3287
  See application file for complete search history.

(56) References Cited

U.S. PATENT DOCUMENTS

| | | |
|---|---|---|
| 4,195,636 A | 4/1980 | Behnke |
| 4,222,380 A | 9/1980 | Terayama |
| 4,270,537 A | 6/1981 | Romaine |

(Continued)

FOREIGN PATENT DOCUMENTS

| | | |
|---|---|---|
| EP | 0 526 986 A1 | 2/1993 |
| EP | 1930038 A2 | 6/2008 |

(Continued)

OTHER PUBLICATIONS

Int'l Search Report issued on Aug. 11, 2010 in Int'l Application No. PCT/US2009/056778.

(Continued)

*Primary Examiner* — Rebecca E Eisenberg
(74) *Attorney, Agent, or Firm* — Panitch Schwarze Belisario & Nadel LLP

(57) ABSTRACT

In accordance with some embodiments of the present invention an automated injection device may be loaded with a standard type syringe and/or hypodermic needle. Optionally the syringe may be supplied loaded with medicine and/or covered with a sterile needle cover. The syringe may be loaded into the injector with in a sterile state with needle cover in place. Injector may include for example a fastener (for example an adhesive base). In some embodiments, the fastener may assist a user to hold injector steady on the skin of a patient for an extended period. For example, injector may be used to give injections of volume ranging between 0.5 and 3.0 ml over a time period ranging between 30 sec to 180 sec.

22 Claims, 21 Drawing Sheets

(52) U.S. Cl.
CPC ... *A61M 2005/2013* (2013.01); *A61M 2207/00* (2013.01); *Y10T 29/49826* (2015.01)

(56) References Cited

U.S. PATENT DOCUMENTS

| | | | |
|---|---|---|---|
| 4,403,987 | A | 9/1983 | Gottinger |
| 4,781,688 | A | 11/1988 | Thoma et al. |
| 5,190,521 | A | 3/1993 | Hubbard et al. |
| 5,478,315 | A | 12/1995 | Brothers et al. |
| 5,662,678 | A | 9/1997 | Macklin |
| 5,766,186 | A | 6/1998 | Faraz et al. |
| 6,200,296 | B1 | 3/2001 | Dibiasi et al. |
| 6,743,211 | B1 | 6/2004 | Prausnitz et al. |
| 7,060,054 | B2 | 6/2006 | Nissels |
| 7,291,159 | B2 | 11/2007 | Schmelzeisen-Redeker et al. |
| 7,740,600 | B2 | 6/2010 | Slatkine et al. |
| 2002/0022798 | A1 | 2/2002 | Connelly et al. |
| 2003/0229308 | A1 | 12/2003 | Tsals et al. |
| 2004/0030353 | A1 | 2/2004 | Schmelzeisen-Redeker et al. |
| 2005/0033234 | A1 | 2/2005 | Sadowski et al. |
| 2005/0101912 | A1 | 5/2005 | Faust et al. |
| 2006/0293722 | A1 | 12/2006 | Slatkine et al. |
| 2007/0270745 | A1 | 11/2007 | Nezhat et al. |
| 2009/0043245 | A1 | 2/2009 | Nguyen |
| 2009/0093792 | A1 | 4/2009 | Gross et al. |
| 2009/0118662 | A1 | 5/2009 | Schnall |
| 2010/0185148 | A1 | 7/2010 | Gillespie, III et al. |
| 2010/0286714 | A1* | 11/2010 | Gyrn et al. ............ 606/139 |
| 2011/0040280 | A1 | 2/2011 | Ijitsu et al. |
| 2011/0166509 | A1 | 7/2011 | Gross et al. |
| 2014/0088509 | A1* | 3/2014 | Sonderegger et al. ....... 604/157 |
| 2014/0249502 | A1 | 9/2014 | Nie |

FOREIGN PATENT DOCUMENTS

| | | |
|---|---|---|
| EP | 2316510 A2 | 5/2011 |
| EP | 2468340 A1 | 6/2012 |
| EP | 2468342 A1 | 6/2012 |
| EP | 2578188 A1 | 4/2013 |
| WO | 03103750 A1 | 12/2003 |
| WO | 2006/016364 A2 | 2/2006 |
| WO | 2006/069380 A1 | 6/2006 |
| WO | 2008034743 A1 | 3/2008 |
| WO | 2012000836 A1 | 1/2012 |
| WO | 2012134588 A1 | 10/2012 |
| WO | 2012145685 A1 | 10/2012 |

OTHER PUBLICATIONS

Int'l Preliminary Report on Patentability issued Mar. 15, 2011 in Int'l Application No. PCT/US2009/056778.
Office Action issued Oct. 17, 2012 in U.S. Appl. No. 13/063,236.
Office Action issued May 23, 2013 in U.S. Appl. No. 13/063,236.
Int'l Search Report and Written Opinion issued Dec. 12, 2014 in Int'l Application No. PCT/US2014/058433.
Int'l Search Report and Written Opinion issued Mar. 2, 2015 in Int'l Application No. PCT/US2014/058446.
U.S. Appl. No. 14/186,403 by Cabiri, filed Feb. 21, 2014.
Office Action issued Oct. 7, 2015 in U.S. Appl. No. 14/186,403 for Cabiri.
Int'l Search Report and Written Opinion issued May 27, 2015 in Int'l Application No. PCT/US2014/058456.

* cited by examiner

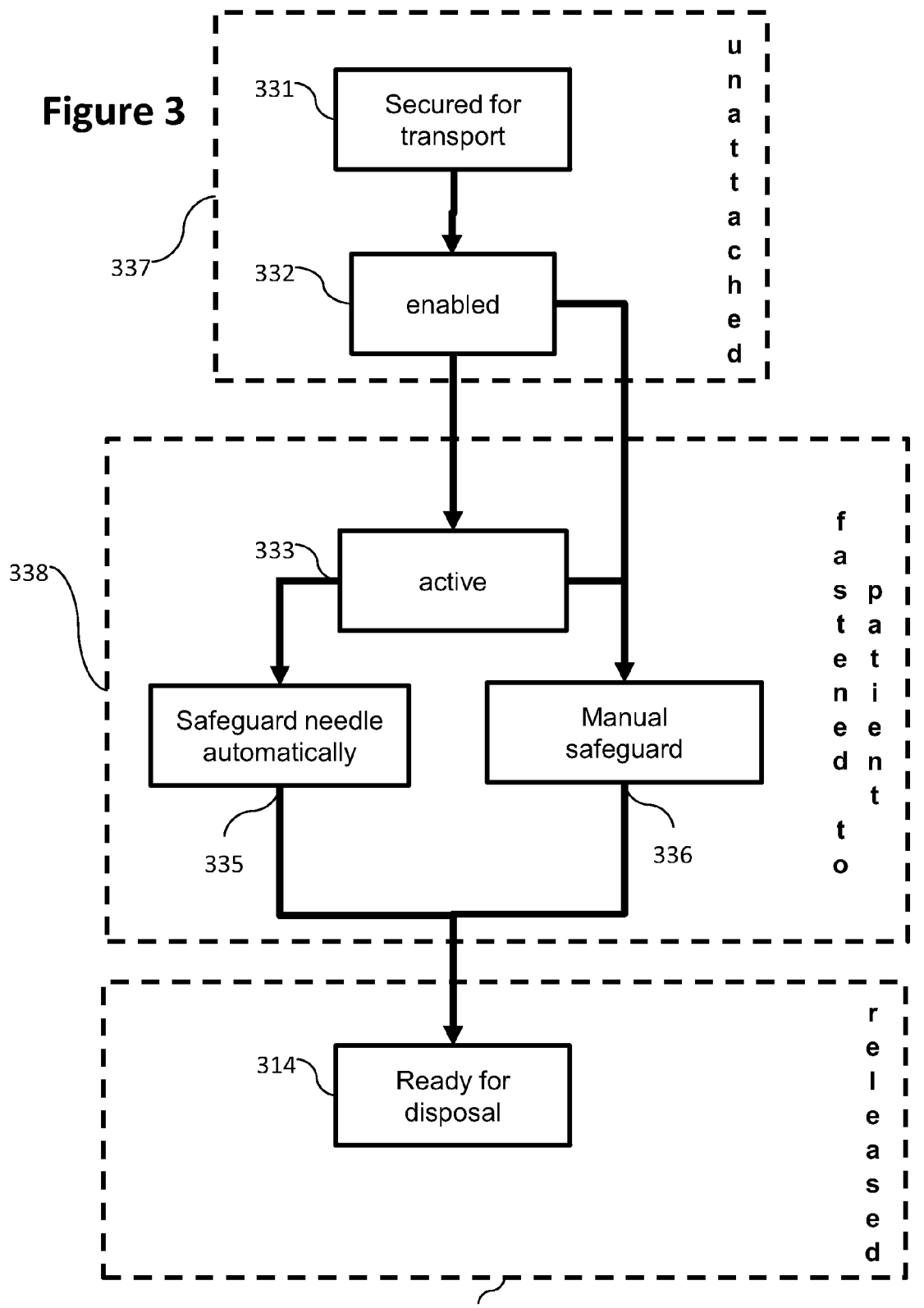

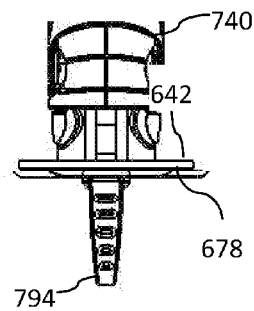
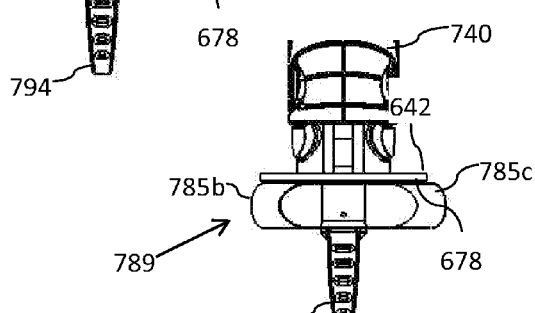
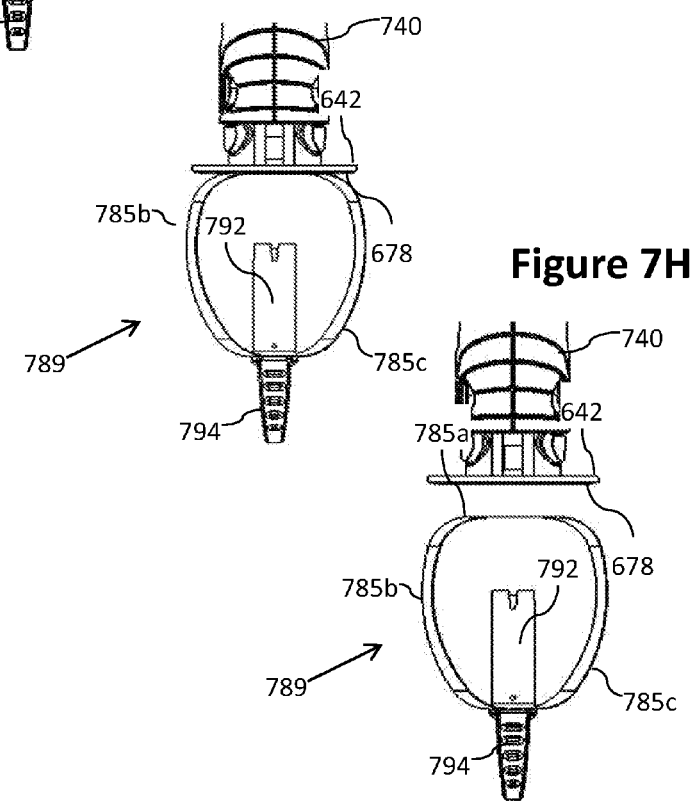

STABILIZED PEN INJECTOR

CROSS REFERENCE TO RELATED APPLICATIONS

This application is a Continuation-in-Part of U.S. patent application Ser. No. 13/063,236 filed Mar. 10, 2011 which is a Section 371 of International Application No. PCT/US2009/056778, filed Sep. 14, 2009 which claims priority to U.S. Provisional Patent Application No. 61/192,198 filed Sep. 15, 2008.

This application claims the benefit of priority under 35 USC §119(e) of U.S. Provisional Patent Application No. 61/884,597 filed Sep. 30, 2013, the contents of which are incorporated herein by reference in their entirety. The contents of all of the above applications are incorporated by reference as if fully set forth herein.

FIELD AND BACKGROUND OF THE INVENTION

The present invention, in some embodiments thereof, relates to a medical injector and, more particularly, but not exclusively, to an injector stabilized for an extended bolus delivery.

International Patent Application Publication No. WO/2013/104414 to SANOFI-AVENTIS DEUTSCHLAND GMBH Describes a guiding assembly for an injection device comprising a mount adapted to receive an injection device, a first gripping member rotatably coupled to the mount, a first lateral stop member coupled to the first gripping member, and a spring biasing the first gripping member in a first angular position.

U.S. Patent Application Publication No. 2011/0166509 to Gross and Cabiri discloses an apparatus for use with tissue of a subject, including a substance configured to be injected into the tissue, and first and second tissue-squeezing surfaces configured to be placed on first and second sides of the tissue, to exert pressure on the tissue by being moved toward each other in response to a squeezing force (F), and to facilitate injection of the substance into the tissue by releasing the substance in response to application of the squeezing force.

U.S. Patent Application Publication No. 2012/0130344 to Ebbett discloses a skin gripping means for use with an injector. In one embodiment the skin gripping means is a needle guard. An exterior surface of the skin gripping means is provided with a plurality of fingers adapted to engage a subject's skin when in use. A method of performing a subcutaneous injection is also disclosed with includes the steps of bringing a skin gripping means of an injector into contact with the skin of a subject, moving the skin gripping means substantially parallel to the skin to thereby form a fold in the skin, moving a needle of the injector into the fold to a suitable position for a subcutaneous injection and injecting a substance through the needle.

U.S. Pat. No. 8,267,890 to Alchas discloses a medication delivery device, particularly an intradermal delivery device, having a needle cannula, with a sharpened distal end having a forward tip, and a limiter disposed about the needle cannula. The limiter has a distal end defining a skin engaging surface which is disposed transversely to, and at least partially about, the needle cannula. The skin engaging surface is generally non-flat with generally coplanar portions, and a recess being defined in the skin engaging surface which defines a void in or adjacent to the coplanar portions into which portions of a patient's skin can be deformed into when the skin engaging surface is pressed against the patient's skin. The forward tip of the needle cannula is spaced apart from a plane defined by the coplanar portions a distance ranging from about 0.5 mm to 3.0 mm such that the skin engaging surface limits penetration of the forward tip of the needle cannula to the dermis layer of the patient's skin.

Additional background art includes U.S. Patent Application Publication No. 2009/093,792 to Gross and Cabiri, U.S. Pat. No. 8,348,898 to Cabiri, U.S. Pat. No. 7,530,964 to Cabiri and U.S. Patent Application Publication No. 2009/0012494 to Yeshurun.

SUMMARY OF THE INVENTION

According to an aspect of some embodiments of the present invention there is provided an autoinjector including: a drug container having a principle longitudinal axis; an adhesive layer which in operation is in contact with a skin of a patient in a vicinity of an injection site and which in operation is attached to the drug container orienting the principle longitudinal axis at an angle between 60 to 120 degrees to the injection site; and a driver for discharging a contents of the drug container into the patient.

According to some embodiments of the invention, in operation the adhesive layer impedes lateral movement of the autoinjector along the skin.

According to some embodiments of the invention, a design stress on the autoinjector is sufficient to remove the adhesive from the skin.

According to some embodiments of the invention, the autoinjector may further include a semi-rigid skirt extending beyond a base of the autoinjector and a portion of the adhesive may be attached to the skirt.

According to some embodiments of the invention, the adhesive does not extend beyond a base of the autoinjector.

According to some embodiments of the invention, the adhesive has an adhesive strength ranging between 500-1500 g.

According to some embodiments of the invention, a height of the autoinjector perpendicular to the adhesive layer is greater than a width of the adhesive layer.

According to some embodiments of the invention, a longitudinal center of gravity of the autoinjector is between 40 to 80 mm from the adhesive layer.

According to some embodiments of the invention, the autoinjector may further include a needle retraction mechanism.

According to some embodiments of the invention, the autoinjector may further include a needle in fluid communication with the drug container. The needle may be rigidly connected to the drug container and in operation at least of portion of the needle may project from the autoinjector into the patient.

According to some embodiments of the invention, the needle includes a straight needle and the needle protrudes from the drug container in a direction substantially parallel to the principle longitudinal axis.

According to some embodiments of the invention, in operation the needle forms a fluid path directly from the drug container into the patient.

According to some embodiments of the invention, the driver is internally powered.

According to some embodiments of the invention, the autoinjector may further include a motor for powering the driver.

According to some embodiments of the invention, the driver is configured for discharging the drug over a time period ranging between 30 seconds and 600 seconds.

According to some embodiments of the invention, in operation, the drug container moves with respect to the adhesive layer in a direction parallel to the principle longitudinal axis.

According to some embodiments of the invention, a volume of the drug container is between 0.5 and 5 ml.

According to some embodiments of the invention, the autoinjector may further include a hypodermic needle and an automatic safeguard mechanism protecting the hypodermic needle at a completion of the discharging and the discharging may be through the hypodermic needle.

According to some embodiments of the invention, the automatic safeguard mechanism includes a needle retractor.

According to an aspect of some embodiments of the present invention there is provided a method of injecting a substance into a patient including: fastening an injector to the patient; moving a medicine container linearly with respect to the injector to insert into the patient a needle rigidly attached to the medicine container, and discharging the substance from the medicine container through the needle into the patient while the injector remains fastened to the patient.

According to an aspect of some embodiments of the present invention there is provided a method of manufacture of a stabilized autoinjector including: installing a syringe rigidly attached to a sterile needle and needle cap into a pen injector having an adhesive stabilizer; and attaching a cover remover to the needle cap through a hole in the adhesive stabilizer.

According to some embodiments of the invention, the discharging is a continuous dose of between 0.5 and 5 ml.

According to some embodiments of the invention, the discharging continues for between 20 and 600 sec.

According to some embodiments of the invention, the fastening includes adhering an adhesive to the patient.

According to some embodiments of the invention, the moving is parallel to a principle longitudinal axis of the medicine container.

According to some embodiments of the invention, the discharging is self powered.

According to some embodiments of the invention, discharging is powered by a motor.

According to some embodiments of the invention, the moving is in a direction at an angle of between 60 and 120 degrees of a surface of a skin of the patient at an injection site.

According to some embodiments of the invention, the installing includes engaging a plunger of the syringe to a power supply.

According to some embodiments of the invention, the method may further include filling the syringe with between 1 and 5 ml of a medicine.

According to some embodiments of the invention, the attaching impedes lateral movement of the injector along the skin.

According to some embodiments of the invention, a design stress on the injector is sufficient to reverse the attaching.

According to some embodiments of the invention, the method further includes peeling the adhesive from the patient by rotating the injector.

According to some embodiments of the invention, the fastening has a strength ranging between 500-1500 g.

According to some embodiments of the invention, the method may further include retracting the needle. Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3 is a state diagram of an injector according to an embodiment of the present invention;

FIGS. 7A-K are detailed illustrations of an alternative stabilized injector according to an embodiment of the present invention;

DESCRIPTION OF SPECIFIC EMBODIMENTS OF THE INVENTION

Figure 1:
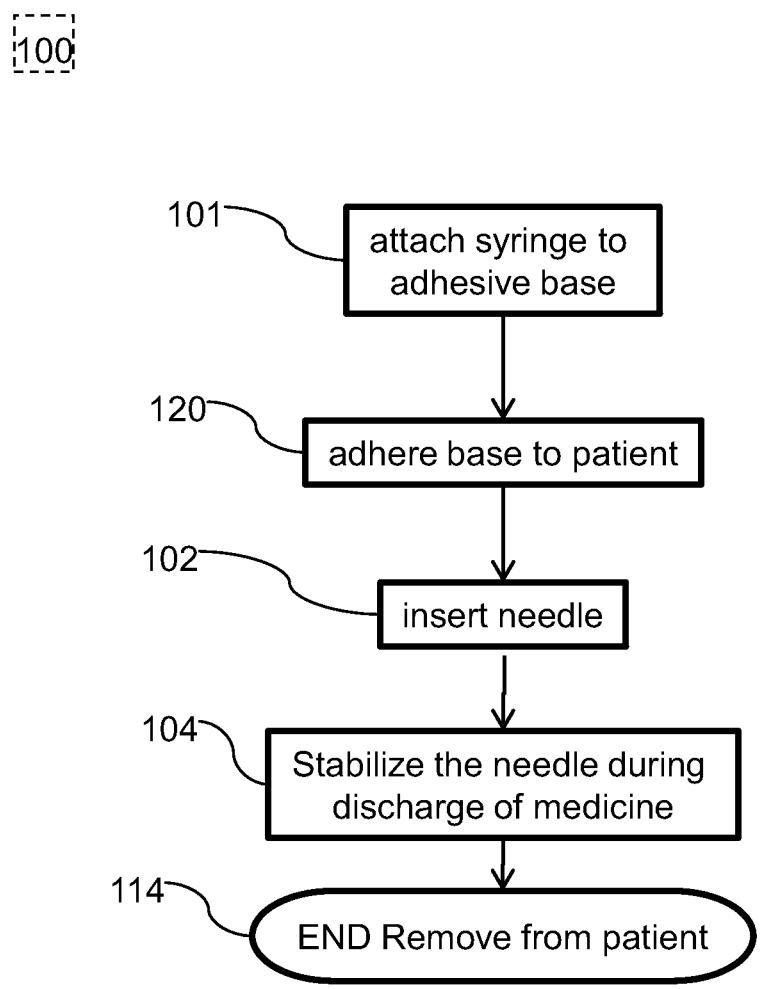
FIG. 1 is a flowchart illustrating a method of stabilizing a needle in a patient according to an embodiment of the present invention.

The present invention, in some embodiments thereof, relates to a medical injector and, more particularly, but not exclusively, to an injector for an extended bolus delivery.

Overview

1 Pen Injector with Stabilizer

An aspect of some embodiments of the present invention relates to an autoinjector and/or pen injector with stabilization. Stabilization may include for example fastening and/or adhering the injector to the skin of a patient. In some embodiments, a stabilized injector may perform injections of larger volumes and/or larger time lengths than a conventional pen injector.

In some embodiments, a pen injector may include a pre-sterilized fluid path. Optionally the fluid path may be inserted into the injector in a sterile and/or protected condition. Optionally a protective cover for the fluid path may be removed by an end user. Optionally the fluid path may be very simple. For example, the fluid path may include a straight needle directly and/or rigidly connected to a drug container. In some embodiments, the needle may be in fluid communication with the drug container, for example as in a standard hypodermic syringe. In some embodiments the needle may have a sterile cover. The needle cover may for example include a standard needle cover. Optionally, the needle may be coaxial to the drug container. Alternatively or additionally the needle may be mounted of center of the drug container. Some embodiments of the invention may include a standard straight needle. Alternatively or additionally, the needle may be bent and/or curved.

In some cases, it may be difficult for a user to manually hold an autoinjector stable. For example the user may find it difficult to hole the injector immobile enough and/or for long enough to complete injection. A stabilized auto injector may include a skin fastener, for example an adhesive, to increase stability of the injector. The fastener may hold and/or assist the user to hold the activation zone of the injector and/or the injection zone and/or a needle aperture and/or a needle stable with respect to the skin of the patient. The pen injector may include and/or perform some or all of the functions of a syringe stabilizer and/or a needle positioner, for example as mentioned herein below.

According to some embodiments of the current invention the payload of the syringe may include, for example between 0.5 and 2 ml and/or between 2 and 4 ml and/or between 4 and 5 ml of a drug and/or more. In some embodiments, the injector may discharge the entire payload as a single dose. For example, a pen injector may include an internally powered driver to drive the plunger and/or discharge the payload. For the sake of this application an internally powered injector driver may be defined as a drive mechanism powered by energy stored at least temporarily within the injector. Power may be stored in a power supply, for instance as chemical potential (for example a chemical that produces an expanding gas and/or a battery) and/or mechanical potential (for example stored in an elastic member and/or a spring and/or a pressurized gas). For example the driver may be designed to discharge the payload over a time period ranging between 20 and 120 seconds and/or between 120 and 600 seconds and/or longer. In some embodiments, discharge may be driven by a driver. An internally powered driver may be powered by various mechanisms including for example a motor (including for example a DC motor, an actuator, a brushless motor) and/or a transmission and/or a telescoping assembly and/or a threaded element and/or a and/or an elastic mechanism (for example a spring and/or a rubber band) and/or an expanding gas and/or a hydraulic actuator).

A pen injector according to some embodiments of the current invention may include a medicine container. For example a medicine container may be a standard type syringe. Optionally a standard type syringe may be loaded with medicine using standard equipment and/or in an aseptic room. A standard type syringe may optionally be preloaded with a medicine and/or include a sterile needle and/or be at least partially protected by a sterile cover for example a needle cover when the syringe is supplied and/or installed into an injector. For example, the medicine container may optionally include a cylindrical barrel rigidly attached to a needle. For example, the barrel and the needle may be oriented coaxially. In some embodiments a plunger may slide axially along the inside of the barrel to discharge a medicine payload.

2 Syringe Stabilizer

An aspect of some embodiments of the present invention relates to a stabilization device for a hypodermic syringe. In some cases, it may be difficult for a user to manually hold a conventional syringe in a proper location and/or immobile enough and/or for long enough to complete injection. This problem may be particularly acute in home treatments where the caretaker may not be highly skilled. This problem may be particularly acute when injecting large volumes of liquid and/or for long periods of time, for example longer than 20 sec.

In some embodiments a syringe may be held stable with respect a fastener, fastened to the skin of a patient. The fastener may stabilize the syringe with respect to the skin of a patient. For example, with stabilization, a non-skilled person may be able to hold a syringe in its proper place for a time ranging between 20 to 600 seconds and/or the syringe may be held substantially immobile with respect to the skin of a patient for a time ranging for example between 60 to 180 seconds. For example the injector may inject of volume of drug ranging between 0.5 to 5 ml.

For example, holding the injector immobile may include preventing straining the needle and/or bending the needle and/or occluding the needle and/or injury the patient in the injection site and/or moving the needle from the intended injection site for example due to shearing forces along the patient's skin and/or forces perpendicular to the patient's skin. In some embodiments, the fastener may be strong enough to prevent lateral movement of the injector (sliding along the skin of the patient) under designated design stresses. In some embodiments, the fastener may be strong enough to hold the injector to the body of the patient without additional support (for example preventing lateral movement and/or longitudinal movement (perpendicular to the skin of the patent) and/or rotational movement with respect to the patient's skin under designated design stresses. Alternatively or additionally, the fastener may assist a user to manually hold the injector to the patient's body.

3 Needle Positioner

An aspect of some embodiments of the present invention relates to a device for positioning a needle in an intended tissue for medical injection. For example, it is sometimes desired to inject a drug into subcutaneous tissue. In some cases locating a conventional needle in the proper tissue can be difficult. For example skin can fold, wrinkle, stretch and/or deform in such a way that it is difficult to locate the correct tissue. In some embodiments of the current invention, an adhesive base is used to hold the skin of a patient in a fixed position. A syringe may be held in a predetermined position with respect to the base such that a needle connected to the syringe pierces the skin and enters a desired tissue.

In some embodiments, a syringe may be held substantially perpendicular to a surface contacting the user's skin. For example, the syringe may be held at an angle ranging between 60° to 120° to the user's skin during injection. In some embodiments an injection may be into subcutaneous tissue. For example the needle length and/or needle insertion depth may range for between 3 to 12 mm. In some embodiments an injection may be into muscle. For example the needle length and/or needle insertion depth may range for between 16 to 25 mm.

4 Flexible Cover to Peel Adhesive Protector

An aspect of some embodiments of the present invention relates to a mechanism to peel an adhesive protector when a safety cover is pulled off of an autoinjector. For example the safety cover may be flexible and/or a hinged and/or may be anchored to an edge of the adhesive cover. For example the safety cover may include a needle cover remover connected to a folded adhesive protector. As the safety cover is pulled away the pulling force may be transferred to a peeling force at one or more edges of the adhesive protector.

5 Rotary Needle Retraction Mechanism

An aspect of some embodiments of the present invention relates to a needle safety mechanism for an autoinjector. Optionally, an unshielded needle may be safeguarded in response to resistance and/or a change of resistance to discharging of the injector payload.

In some embodiments a change in resistance to discharging may activate a rotary needle protector. For example, a resistance to discharging may engage a pair of threaded elements. Optionally, a drive may power discharging of a drug. The drive may drive a relative rotation between the pair of threaded elements. Relative rotation of the threaded elements may, in some embodiments, activate needle protection. For example, relative rotation of the pair of threaded elements may cause retraction of the needle.

In some embodiments, a lock may hold a needle in an unshielded position. The lock may optionally act as a support for a discharge driver. Increasing resistance to discharge may increase the stress on the driver. When the stress on the driver increases beyond a threshold and/or decreases beyond a threshold the lock may be released and/or the needle retracted to a safe location. For the sake of the current disclosure retraction of a needle may include pulling a needle point back into a shielded location without changing the length and/or shape of the shielding; and/or retracting may include extending the housing of the injector and/or a shield ahead of a needle point such that the needle is left in a shielded location.

In some embodiments, a support for a needle assembly may include a telescoping assembly. Optionally, the telescoping assembly may retract the needle (for example by contracting) in response to a stress from a driver.

In some embodiments, the safeguarding mechanism may include a sensor sensitive to a linear force from the driver. For example, a pushing force passes a threshold; a lock may be released moving the needle to the retracted configuration.

In some embodiments, the force to insert the needle to the skin of a patient may range for example between 0.02 to 0.2 N and/or between 0.2 and 0.5 N. Optionally, the force required to inject the drug (for example the force on a syringe plunger) may range for example between 5 to 60 N. For example the force required to inject the drug may depend on the injection rate and/or the viscosity of the drug and/or the syringe geometry and/or the needle dimensions.

In some embodiments a needle protection mechanism may be triggered by a linear force greater than, for example, between 10 to 60 N.

For example, an autoinjector may be activated by manually pushing with enough force to insert the needle. The device may then apply an injection force to inject a drug. Once the entire drug is injected and/or when there is an obstruction and/or occlusion, the injection force may rise until it passes a threshold triggering safeguarding of the needle and/or ending injection.

For example in the event of an occlusion and/or at the end of delivery, the linear force generated by the device may increase to the level of up to 60 N. A needle safeguarding mechanism may include a sensor that is sensitive to the force. For example the sensor may include a snap that gives way at 40 N returning the needle to the retracted position.

In some embodiments, the stress to inject a medicine and/or to trigger safeguarding of a needle may include a torque. For example, injection of medicine may be driven by a plunger. The plunger may optionally be driven by a threaded assembly, for example a threaded screw and/or teeth and/or a telescoping assembly. Optionally the pitch of the teeth and/or an associated screw may range for example between 0.5 and 2 mm. The diameter of the screw may range for example between 3 and 15 mm. The torque to power injection may range for example between 0.2 and 1.0 N*cm. The trigger torque (the torque at which the needle safeguarding is triggered) may range for example between to 0.5 to 2 and/or from 2 to 4 and/or from 4 to 10N*cm.

In some embodiments a safety mechanism may include linear movement of the ranging between 5 to 15 mm. For example movement of the safety mechanism may include extension of a needle during insertion and/or retraction of the needle and/or extensions of a safety shield and/or retraction of a safety shield. Optionally a needle insertion length (for example the length of needle inserted into a patient) may range for example between 3 to 12 mm.

During injection, the linear movement of a plunger may range for example between 10-50 mm. The length of movement of the plunger may vary for example with the volume of medicine to be injected that may range for example between 0.5 to 3 ml.

In some embodiments, a sensor of a safeguarding mechanism may be sensitive to a torque. For example, the needle may be retracted when the mechanism is exposed to a twisting moment. Optionally, discharge may be driven by a torque. For example the driver may apply torque to threaded element pushing a plunger. When the torque on the driver reaches a threshold value, the needle may be released and/or retracted and/or a needle shield may be deployed. Alternatively or additionally the trigger mechanism may require both a torque and a linear force. For example, requiring both a torque and a linear stress may prevent premature activation due to momentary friction.

In some embodiments an interference element (for example a snap) may provide resistance to retraction. For example, an annular ring may impede contraction of a telescoping assembly. Alternatively or additionally a rib may impede twisting of a support structure. When stress from the driver passes a threshold, the stress may optionally overcome the interference element. Overcoming the interference element may for example reverts the support to a retracted configuration.

In some embodiments, a stress resulting from resistance to discharge may trigger deployment of a needle shield. The needle shield may optionally move to shield the needle in reaction to the increased stress.

In some embodiments, the retraction mechanism may include a rotary drive. For example, threaded element may raise the needle. For example a motor may drive a plunger injecting a drug (for example by means of a threaded plunger driving assembly). Upon triggering of the release mechanism the same motor may optionally rotate a second threaded assembly retracting the needle.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Embodiments

1 Method of Positioning and/or Stabilizing a Needle

Referring now to the drawings, FIG. 1 illustrates a method of positioning and/or stabilizing a hypodermic needle according to an embodiment 100 of the present invention. In the method an adhesive base is used to retain the skin and/or hypodermic tissue of a patient in a predicable geometry. A syringe retainer holds a syringe in a predetermined position with respect to the base such that a needle mounted to the syringe penetrates the skin to reach a desired tissue. A medicament may optionally be discharged to the desired tissue. The syringe and/or needle may optionally be held in place for an extended period, for example, for a long injection ranging between 30 seconds and 500 seconds. Optionally, an injection could include a large dose for example between 0.5 and 5 ml.

In some embodiments a syringe may be attached 101 to an adhesive base. The attachment may have fixed position and/or the syringe may be movable attached to the base. For example, the attached syringe may move longitudinally between a storage position wherein a needle is shielded by the base and an exposed position wherein a portion of the needle protrudes past the base.

In some embodiments, the base may be adhered 120 to the skin of a patient. Optionally the needle may be attached to the base either before or after adhesion 120 to the skin.

In some embodiments, a needle may be inserted 102 into the skin of the patient. For example, the needle may be inserted 102 by means of a longitudinal movement pushing a portion of the needle into a deployed position point past the base (for example through a hole in the base) into the patent. Optionally, the syringe may be fixedly attached to the base with the needle protruding beyond the adhesive such that placing the adhesive onto the patient also inserts the needle into the patient.

Optionally the device may stabilize 104 in a desired position during discharge of a medicine. When discharge of the medicine finishes, the needle may be removed 114 from the patient and/or the adhesive base may be peeled from the skin. For example, the entire device may be twisted such that one side of the adhesive is lifted and/or peeled from the skin while the far edge of the base of the injector remains in contact with the skin and serves as a fulcrum.

2 Method of Injecting a Drug

Figure 2:
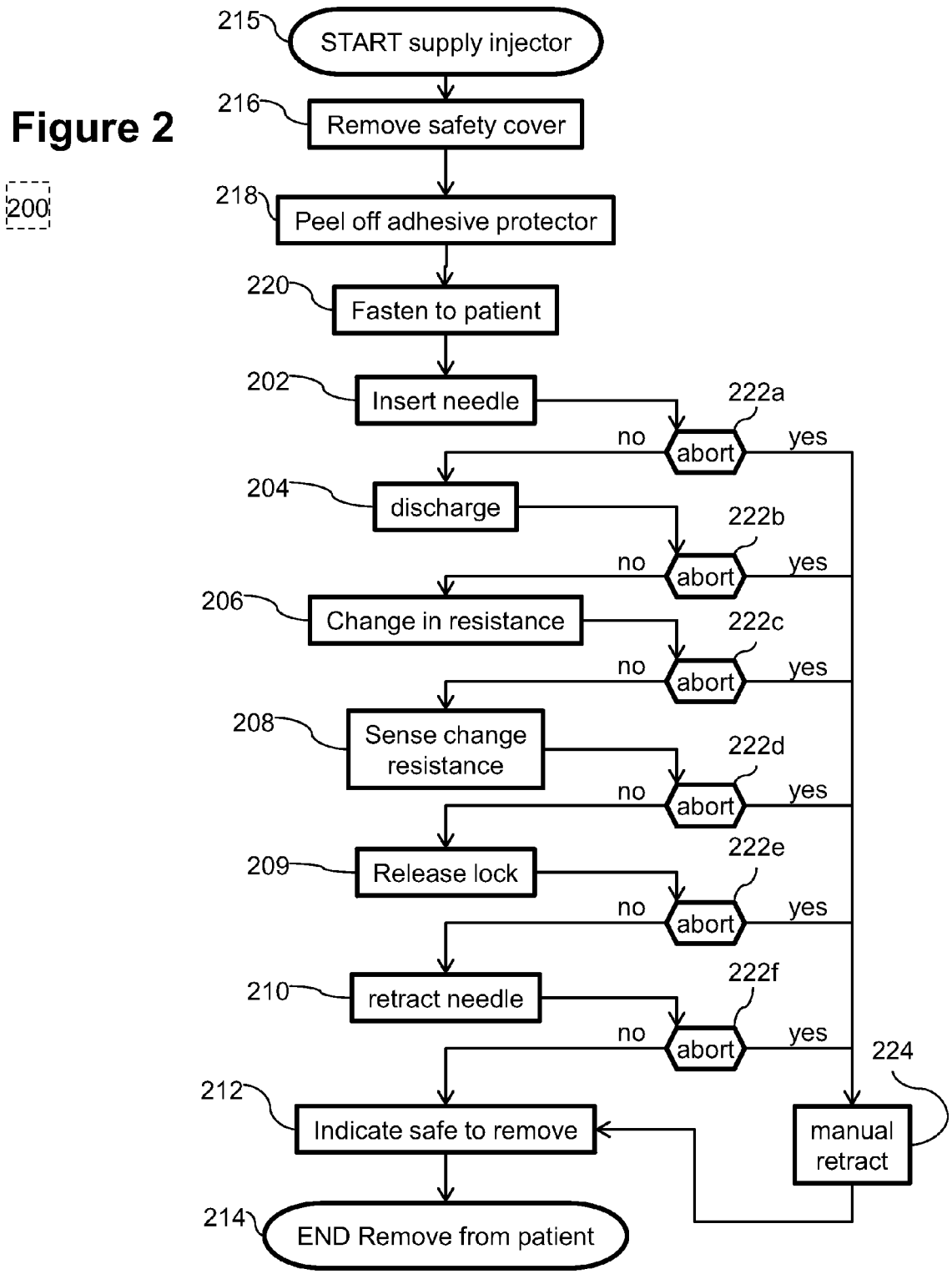
FIG. 2 is a flowchart illustrating a method of injecting a substance according to an embodiment of the present invention.

Referring now to the drawings, FIG. 2 illustrates a method of injecting a drug according to an embodiment 200 of the present invention. In the exemplary method, a needle is optionally held stable while a drug is dispensed to a patient (dispensing a drug may include discharging a drug from the injector).

In exemplary embodiment 200 a user (for example a patient and/or a medical aid in home care) may be supplied 215 with an autoinjector ready to administer a medicine.

The user may optionally remove 216 a safety cover from the injector. Removing 216 the cover may optionally include removing a sterile cover from a needle. Removing 216 the cover may optionally automatically peel 218 an adhesive protector from an adhesive. For example, the adhesive may be supplied to stabilize the injector on the skin of a patient during injection. The injector may optionally be fastened 220 to a patient (who may be the user). In some embodiments a user may hold the injector to the skin of a patient; the fastening 220 may stabilize the injector for example from shifts and/or movements of the patient and/or the user.

In some embodiments, the user may set off an activation mechanism. The activation mechanism may for example insert 202 the needle into the patient, for example by extending the needle outward. For example, a syringe may be moveably attached to the base. A syringe may optionally be rigidly attached to the syringe. For example the syringe may slide linearly along its axis. Sliding the syringe towards the base may cause the needle rigidly to protrude beyond the base. For example, part of the needle may pass through a hole in the base and pierce the skin of a patient. The adhesive of the base may hold the skin of the patient steady while the needle pierces the skin. The combination of an adhesive holding the skin and moving the needle to a predetermined position past the base may facilitate the inserting 202 of the needle into the skin to the desired depth.

The needle may optionally be locked in the extended position. Optionally, the needle may be biased to a protected position (for example to retract into a housing of the injector). Alternatively or additionally, the needle may be biased to the unshielded position. Alternatively or additionally, the autoinjector may be supplied with the needle in an extended mode and/or protected by a cover.

At a point during the injection process, an optional manual retraction 224 mechanism may be used to place the injector in a safeguarded mode. For example, when the user decides to abort 222*a-f* at a point in the process (for example when he detects some sort of malfunction and/or feels a negative reaction to the medicine) the user may manually retract 224 the needle. Optionally there may be an indicator to indicate 212 whether the needle was automatically retracted 210 and/or whether needle was manually retracted 224. Alternatively or additionally there may be an indicator whether a full dose was administered and/or how much medicine was administered.

Once the needle is inserted into the patient, the injector may optionally begin discharging 204 medicine. For example the medicine may be injected through the needle into the patient. Optionally, discharge may continue until a full dose of the medicine is administered.

In some embodiments, after administration of a full dose of the medicine, there may be a change 206 in resistance to further discharging. For example in a syringe based injector, a plunger may reach the end of the syringe and cease to move increasing resistance. Alternatively or additionally, after discharging the entire dose a transmission may be disconnected (for example a threaded element may pass the end of its threading) reducing resistance. Alternatively or additionally, the change 206 in resistance may result from a another cause for example increased resistance due to a full or partial occlusion of a fluid pathway and/or jamming of a mechanical component (for example cross threading of a screw). The change of resistance may optionally be sensed 208 triggering retracting 210 of the needle.

In some embodiments, the needle may be locked in an unshielded state by a force sensitive lock. When the lock senses 208 the change 206 in resistance, it may release 209 the needle which may be retracted 210 to a shielded position.

In some embodiments, a flag may be supplied (for example a LED and/or a changing color indicator) to indicate 212 to the user that the needle has been retracted 210 and/or that the injector can safely be removed 214 from the patient and/or that a fastener has been released. For example, if the injector is adhered to the patient, it may be peeled off and/or a fastener may be released.

3 States of an Autoinjector

FIG. 3 is a state diagram of an autoinjector according to an embodiment of the present invention. In general, may be supplied in an unattached 337 state. An unattached 337 autoinjector may have a secured 331 state. For example in the secured 331 state the injector may be safe to handle and/or transport. Optionally the injector may have an enabled 332 state. For example, in the enabled 332 state, the injector may be unstable and/or easily activated. For example, an injector may be switched from the secured 331 state to the enabled 332 state by removing a needle protector and/or an adhesive cover.

Once activated the injector may optionally be fastened to a patient. In the fastened 338 state the injected may optionally be activated. For example, while the injector is in the active 333 state, a needle may project from the injector. In some embodiments the injector may be hazardous to handle in the enabled 332 and/or active 333 state.

In some embodiments, after use (optionally whether or not administration of the full dose was successful) the user may want to remove and/or dispose of the autoinjector. In some embodiments, it may be difficult and/or dangerous to remove an injector in the enabled and/or active state. For example, when an injector is fastened to a patient by an adhesive, it may be difficult to remove the needle by pulling the injector away from the skin. Optionally, first a needle may be retracted from the skin into the injector. Subsequently the adhesive may be removal by peeling from the skin. In some embodiments, the injector may automatically be safeguarded 335 for example by retraction of a needle upon completion of injection. Alternatively or additionally, the user may have the option to manually secure the injector into a safeguarded 336 state. For example, the optionally of manually needle retraction may avoid the situation where a patient may not be able to properly remove the injector due to a malfunction that leaves the injector fastened to the skin with the needle inserted into the patient. During and/or after safeguarding 335, 336 the injector may be removed from the patient.

Optionally, the injector may have a final released state 339, for example wherein the needle is retracted back into the injector and/or the needle tip is shielded and/or the injector has been unfastened from the patient. Optionally one or more indicators may be supplied to indicate the state of the injector and/or the quantity of medicine discharged. Once released, the injector may be in final 214 state (protected from hazards and/or ready for disposal, for example in a municipal waste).

4 Fastening via Clasping

Figure 4A:
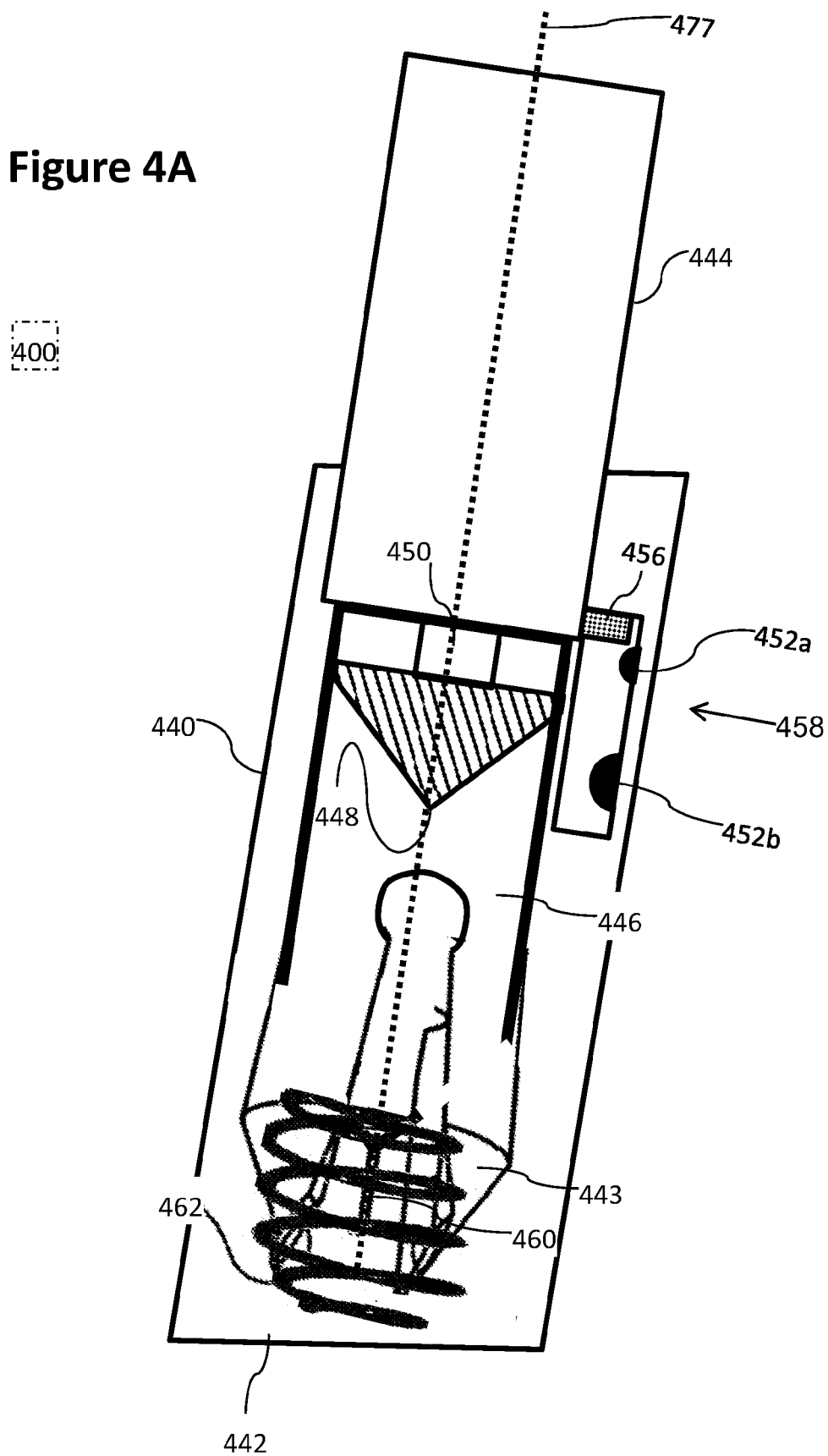
FIGS. 4A-C are schematic illustrations of a stabilized injector according to an embodiment of the present invention.
Figure 4B:
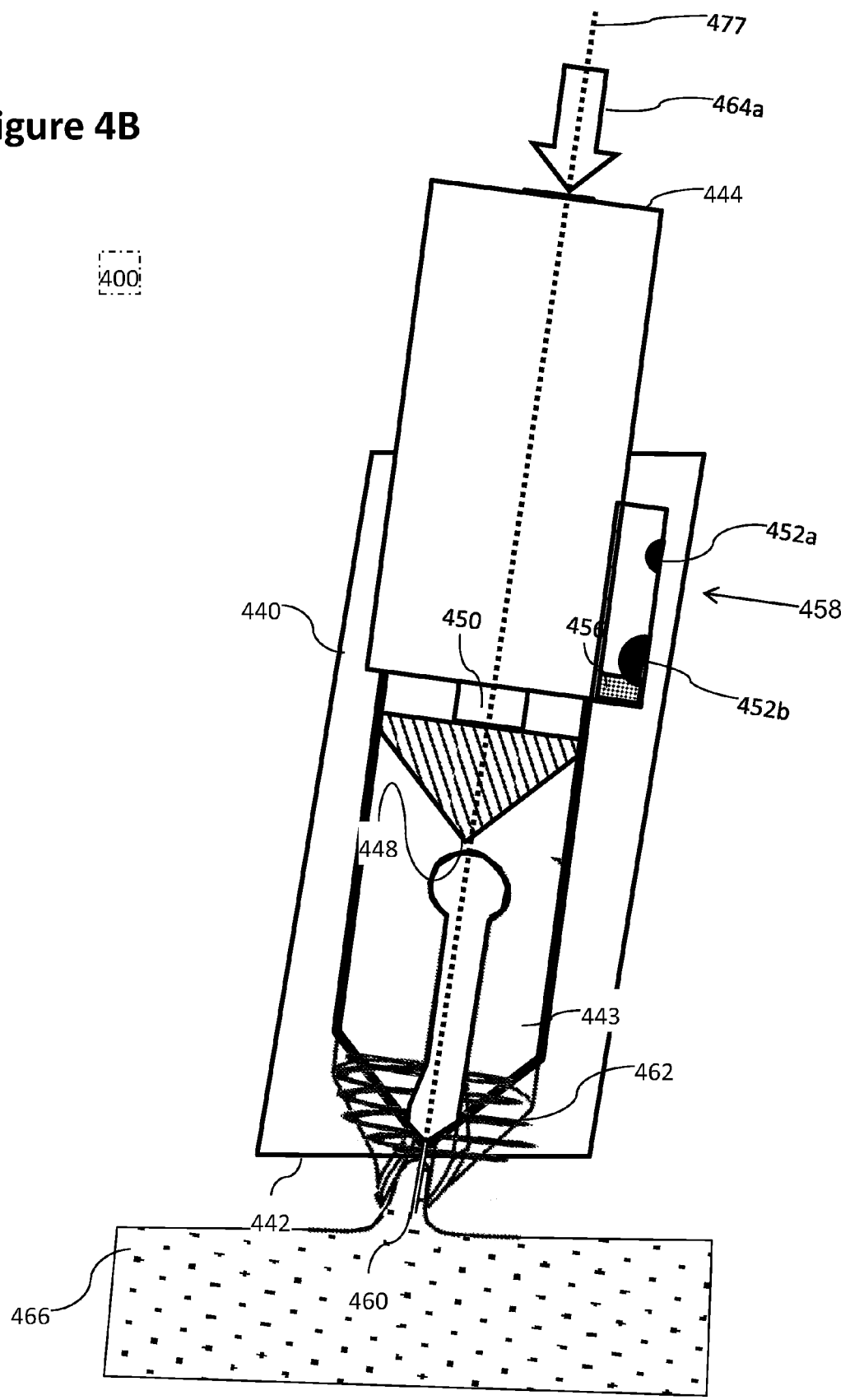
Figure 4C:
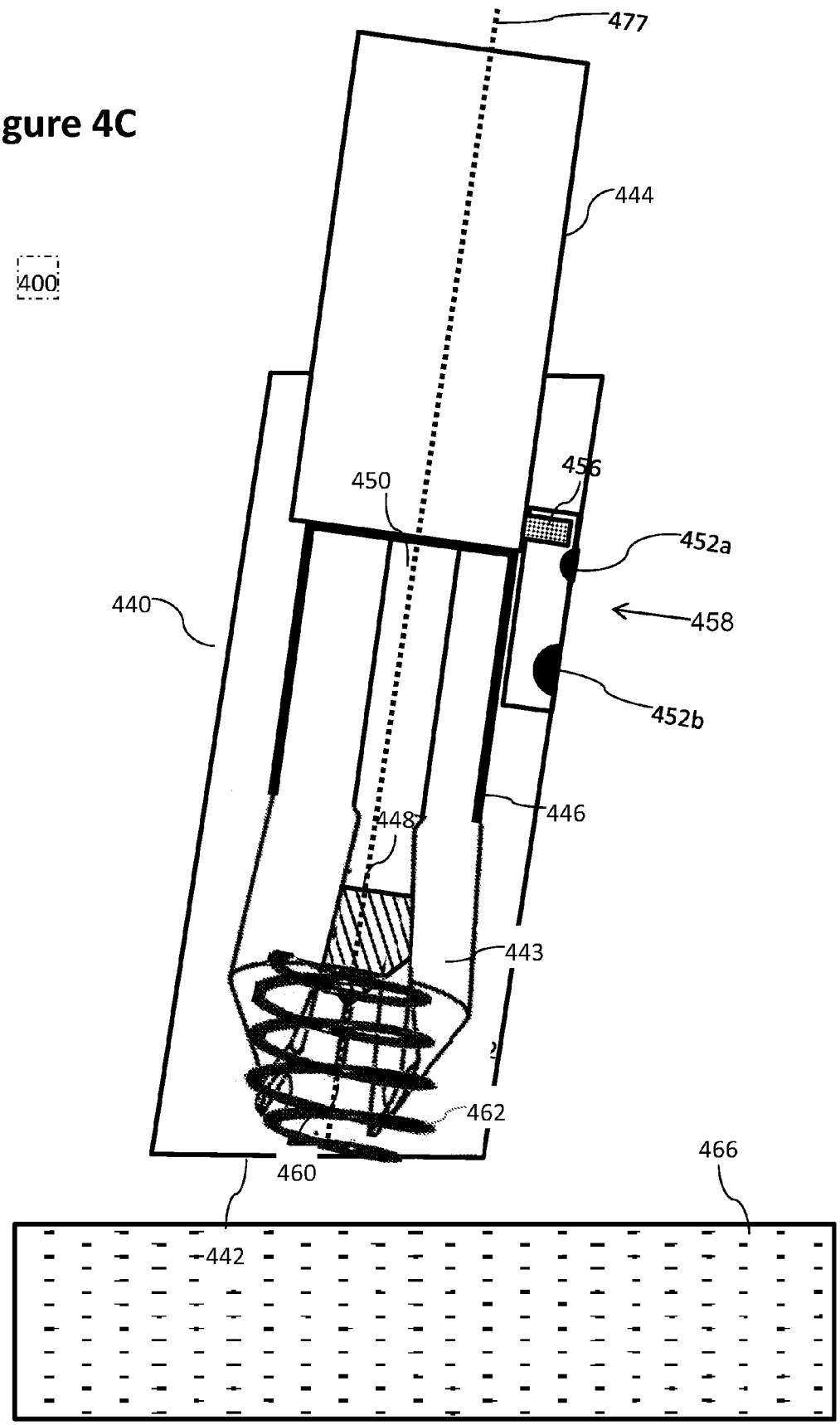

FIGS. 4A-C are schematic illustrations of a needle stabilizing mechanism that clasps the skin of a patient according to an exemplary embodiment 400 of the present invention. In exemplary embodiment 400, a needle 460 is biased to a retracted state for example by a spring 462 (see for example FIG. 4A). In the retracted state, an optional clamp 443 may be biased in an open state.

During injection (for example as illustrated in FIG. 4B) needle 460 is optionally held in an extended state by a driver 444 and/or a medicine container 446. In the extended state, clamp 443 may close onto the skin of a patient holding the injector steady. For example needle 460 may be in fluid communication with medicine container 446.

In some embodiments, at the end of injection driver 444 may retract and/or release medicine container 446 and/or the needle 460. For example driver 444 may be unlocked. Once unlocked, driver 444 may optionally revert to a retracted state and/or clamp 443 may optionally be released and/or needle 460 may optionally retract back into the housing (for example as illustrated in FIG. 4D).

In some embodiments locking mechanism may include for example interference elements 452a,b and/or a locking pin 456 to retain driver 444 in a retracted and/or extended position until a force is applied. For example pin 456 may be rigidly connected to driver 444. In order to move driver 444 from the retracted position (for example as illustrated in FIGS. 4A and 4C) to the extended position (for example as illustrated in FIG. 4B) or back, a force may be applied to push pin 456 past interference elements 452a,b.

FIG. 4A illustrates exemplary embodiment 400 in an enabled state prior to activation. For example, in the enabled state an optional safety cover and/or a sterile cover may and/or an adhesive protector may have been removed from the injector. In the enabled state a needle 460 is shielded by an activation zone on a base 442 of a housing 440. Needle 460 is safeguarded by a retraction assembly including for example a spring 462 biasing the needle into housing 440 and a needle locking mechanism 458 and a driver 444 which hold needle 460 and its supporting medicine container 446 inside housing 440.

FIG. 4B illustrates exemplary embodiment 400 in an activated state, for example right before and/or at the beginning of discharge of a medication. For example, embodiment 400 is activated by pushing driver 444 with a sufficient force 464a. Pushing driver 444 optionally pushes needle 460, medicine container 446, and/or clamp 443 from the retracted position (illustrated in FIG. 4A) to the extended position (illustrated in FIG. 4B). Movement may, for example, be along the primary longitudinal axis 477 of medicine container 446. Optionally, needle 460 is shown coaxial to medicine container 446. Alternatively or additional a needle may be mounted off center of a syringe. As clamp 443 moves from the retracted to the extended position, it closes, grasping a skin 466 of the patient.

In some embodiment, once activated, driver 444 may apply a force on plunger rod 450 and/or plunger 448 to discharge medicine. Optionally driver 444 may be configured to drive discharge of the medicine over a relatively long period of time, for example between 30 to 120 seconds and/or between 120 to 600 seconds.

FIG. 4C illustrates exemplary embodiment 400 at the end of discharge of a medicament. Plunger 448 has optionally reached the end of its path. For example, a locking mechanism 458 has been released. Unlocking locking mechanism 458 may optionally trigger releasing clamp 443 and/or safeguarding needle 460.

5 Adhesive Syringe Stabilizer

Figure 5:
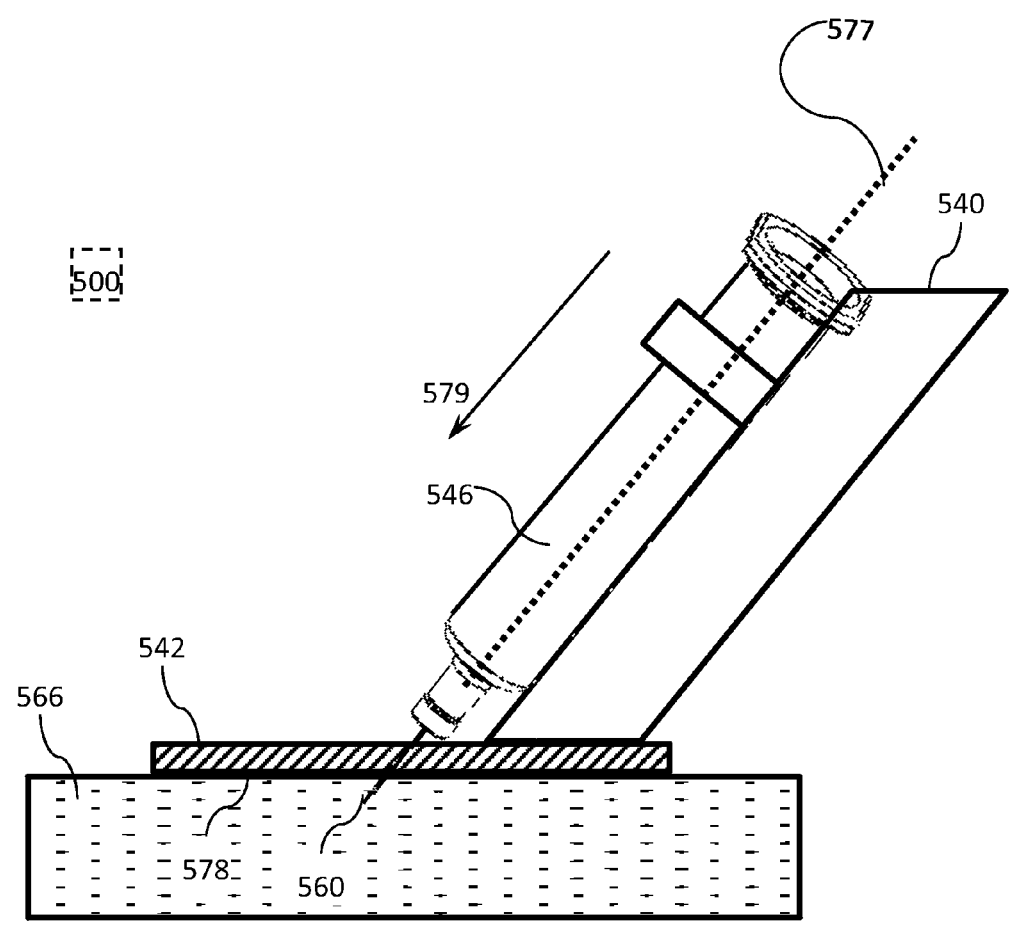
FIG. 5 is a schematic illustration of a needle stabilizer according to an embodiment of the present invention.

FIG. 5 illustrates an adhesive syringe stabilizer 500 according to an embodiment of the current invention. Syringe stabilizer 500 includes a base 542 adhering to a skin of a patient. A syringe 546 is attached to base 542 by means of a housing 540. Syringe 546 is rigidly connected to a needle 560 which protrudes from syringe 546 past base 542 into a skin 566 of a patient. In operation, needle 560 may be in fluid communication with syringe 546 and/or the patient. Needle 560 is shown in embodiment 500 mounted coaxially to syringe 546 (along the principal longitudinal axis 577 of syringe 546). Optionally, needle 560 may be mounted to the syringe off center. In the present application, the term principle longitudinal axis of a drug container may be used to refer to the longest axis of symmetry of the drug container.

In some embodiments, an adhesive 578 may be attached to a distal surface of a base 542. A housing 540 attached to a proximal side of base 542 may optionally hold syringe 546 with a needle 560 protruding from syringe 546 across base 542 (for example through a hole in base 542).

In some embodiments, syringe 546 may be attached to base 542 prior to adhering base 542 to a patient. The entire assembly may be attached to the patent (piercing the skin 566 with needle 560 and inserting needle 560 into the skin until adhesive 578 contacts skin 566).

In some embodiments, syringe 546 may be movably attached to housing 540. For example, syringe 540 may slide longitudinally along housing 540. Optionally, syringe 546 may be attached to housing 540 with needle 560 held proximal to base 542. Then the distal surface of base 542 may be adhered to skin 566. Subsequently, syringe 546 and needle 560 may be slide longitudinally in the distal direction 579 until needle 560 protrudes through base 542 into skin 566. Once needle 560 has been inserted into skin 566 adhesive 578 may assist a user to steady syringe 546 as he discharges medicine into the patient (for example by pushing on a plunger).

In some embodiments, base 542 may first be attached to the patient. Then a user may hold syringe 546 in his hand and insert needle 560 through a hole in base 542 into the skin of the patent. A possible advantage of inserting needle 560 into skin 566 after attaching base 542 to skin 566 is that adhesive 578 may inhibit deformation of skin 566 during needle insertion. This may make it easier to control the precise depth of insertion. After needle 560 has been inserted syringe 546 may be attached to housing 540. Adhesive 578 may assist a user to steady syringe 546 as he discharges medicine into the patient (for example by pushing on a plunger).

6 Detailed Illustration of States of an Injector

FIGS. 6A-D include detailed cross sectional side views illustrating four states of an autoinjector according to an embodiment of the present invention. In some embodiments, an injector 600 is an automated self injection device. For example the self injecting device may in some ways be similar to a pen injector. Optionally injector 600 may be loaded with a standard type syringe 646 and/or hypodermic needle 660. For example, needle 660 may be rigidly connected and/or project from a distal end of syringe 646. Needle 660 may be coaxial with syringe 646. Alternatively or additionally the axis of needle 660 may be parallel to the primary longitudinal axis 677 of syringe 646 but offset therefrom. Syringe may be loaded into injector 600 with needle 660 in a sterile state and/or covered by a sterile cover.

In some embodiments, an injector may include for example an adhesive 678 base 642. For example, adhesive 678 base 642 may assist a user to hold injector 600 steady on the skin of a patient for an extended period. For example, injector 600 may be used to give injections of volume ranging between 0.5 and 3.0 ml over a time period ranging between 30 sec to 180 sec.

Injector 600 includes for example an annular snap resistance element 652 paired to an annular driver support 656. When a linear stress increases past a threshold, the annular snap gives way and a needle 660 may optionally be retracted to a protected location.

Figure 6A:
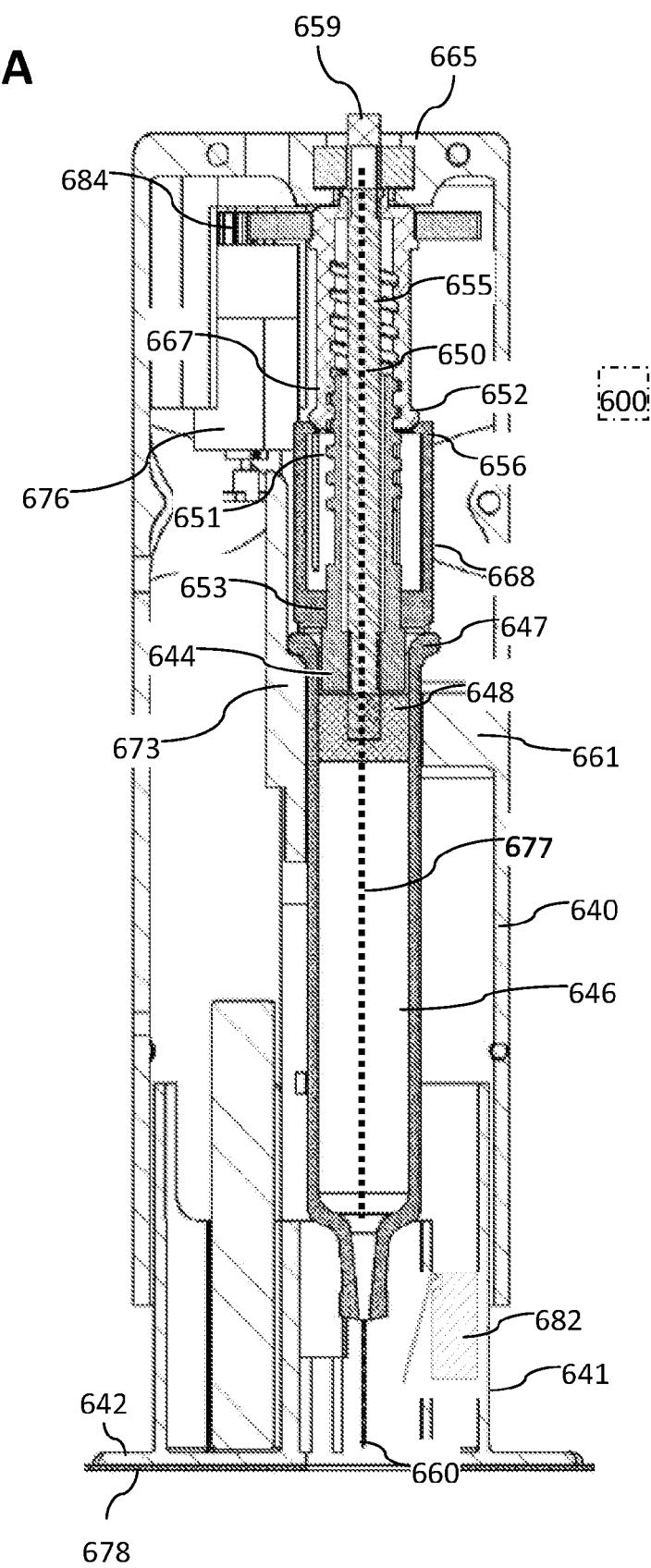
FIGS. 6A-F are detailed illustrations of a stabilized injector according to an embodiment of the present invention.

FIG. 6A is a schematic cross sectional side view illustrating injector 600 in an enabled state (ready for activation). For example, in the enabled state an optional safety cover and/or a sterile cover may and/or an adhesive protector may have been removed from the injector. In the enabled state needle 660 is in a protected location, created by a shield 641 which extends the distal end of a housing 640 of the injector. Needle 660 and/or shield 641 may optionally be retained in position, for example by a snap and/or held in position by a biasing device, for example a spring.

In some embodiments, needle 660 may optionally be supported by a syringe 646; which is in turn supported for example by a cylindrical outer sleeve 668. Outer sleeve 668 may optionally be supported by an annular support 656 resting on an annular snap resistance element 652. For example annular snap resistance element 652 may extend radially outward from a cylindrical inner sleeve 667. Optionally, inner sleeve 667 and/or outer sleeve 668 and/or a driver 644 may be operationally linked to a transmission 684 such that rotating transmission 684 rotates one or more of inner sleeve 667 and/or outer sleeve 668 and/or a driver 644.

In some embodiments, a motor switch 682 may be located in shield 641. In the enabled state (before activation), switch 682 is optionally switched off.

In injector 600, syringe 646 is held to outer housing 640 by a socket 661. Socket 661 allows syringe 646 to slide axially with respect to housing 640 but not to move laterally. In injector 600, transmission 684 is held rotatably fixed to housing 640 by bearing 659 in a hub 665.

Figure 6B:
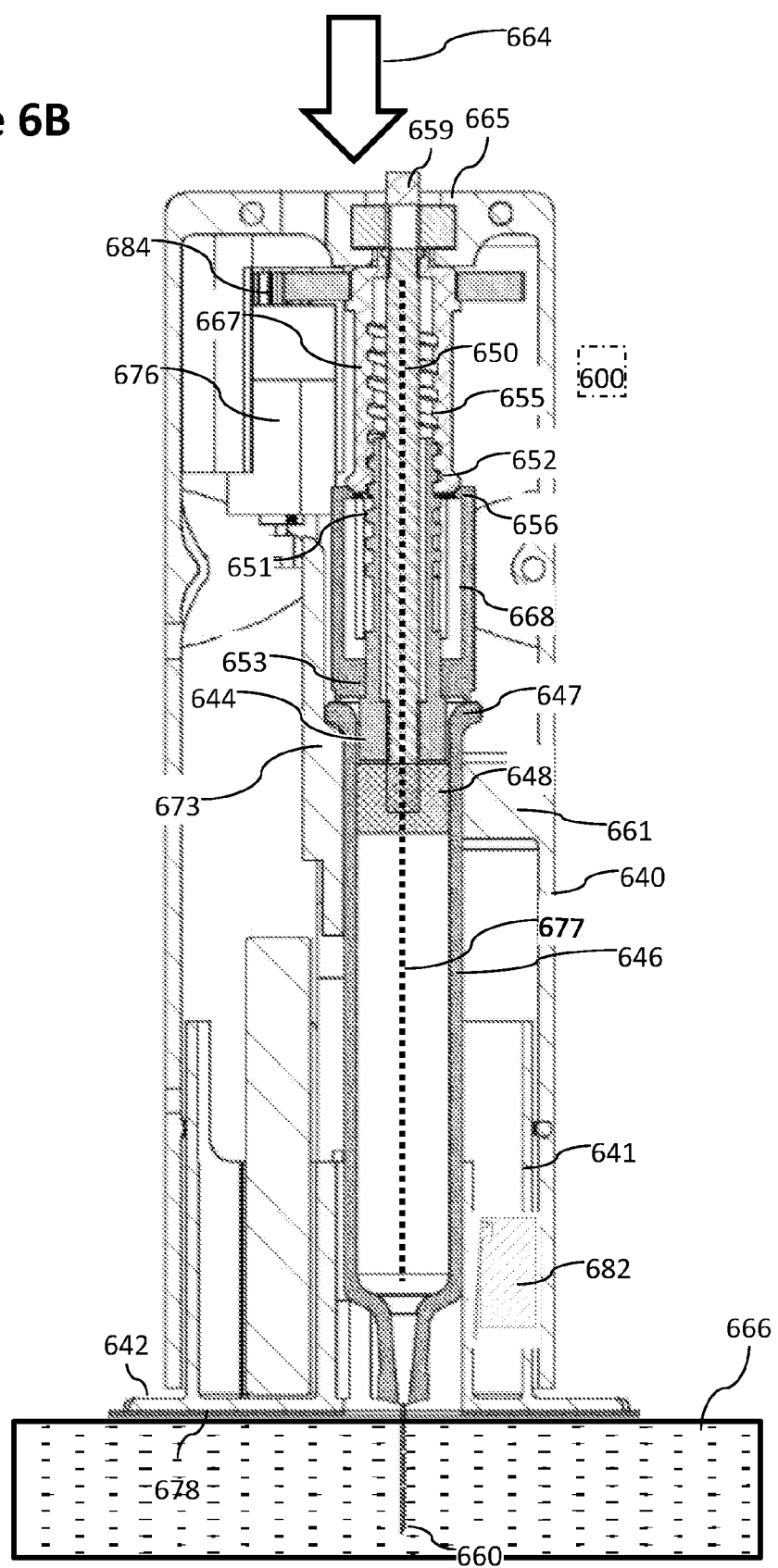

FIG. 6B is a schematic cross sectional side view illustrating injector 600 immediately after activation. For example, to activate the injector, a user may place the distal end of the injector (including for example an adhesive 678 and/or an activation zone on base 642) against the skin 666 of a patient and/or push 664 on the proximal end of the injector until shield 641 collapses into housing 640 in a direction parallel to the longitudinal axis of needle 660. Collapse of shield 641 may optionally unshield needle 660 tip which may for example be pushed into the skin 666 of the patient. For example, in operation, needle 660 may protrude from injector 600 into a patient. Optionally, in operation, needle 660 may be in fluid communication with syringe 646 and/or the patient. For example needle 660 may supply a fluid pathway for discharging medicine directly from syringe 646 through needle 660 into the patient.

In some embodiments, collapse of shield 641 may activate switch 682. For example in injector 600 switch 682 is depressed by being pushed against syringe 646. Depressing switch 682 may activate a motor 676 to start discharging a drug. For example, in injector 600 motor 676 turns a transmission 684. Transmission 684 may include for example a gear. Transmission 684 may optionally rotate inner sleeve 667 and/or driver 644. In exemplary injector 600, driver 644 includes teeth and/or threads which engage a screw thread 653 on a plunger rod 650. Rotating driver 644 may optionally drive plunger rod 650 and/or plunger 648 in the distal direction, discharging the medicine. Optionally, plunger 648 continues to move distally until it is stopped by for example a blockage in the fluid path (preventing further discharge) and/or until plunger 648 reaches the distal end of syringe 646. Optionally, when needle 660 is in the extended position, a flange 647 of syringe 646 seats against a bracket 673, which holds syringe 646 and/or prevents further longitudinal movement.

Figure 6C:
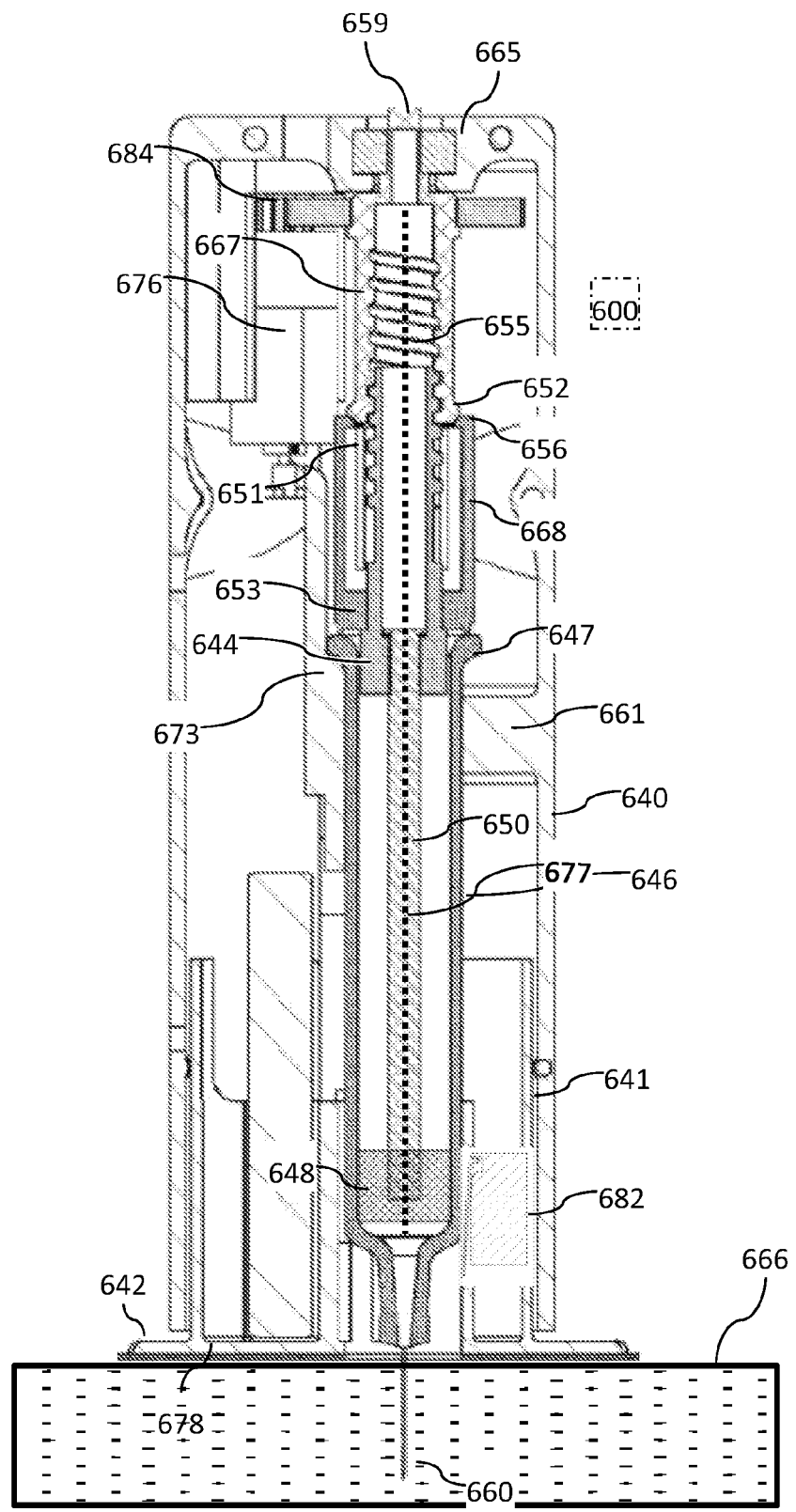

FIG. 6C is a schematic cross sectional side view illustrating injector 600 at the end of discharge of the payload. For example plunger 648 has discharged all of the medicine out of syringe 646 and/or has reached the distal end of syringe 646. Optionally, further rotation of driver 644 increases the stress pushing driver 644 proximally. Interference element 652 may serve as stress sensor. For example, motor 676 may supply enough torque to create a force which overcomes interference element 652.

Figure 6D:
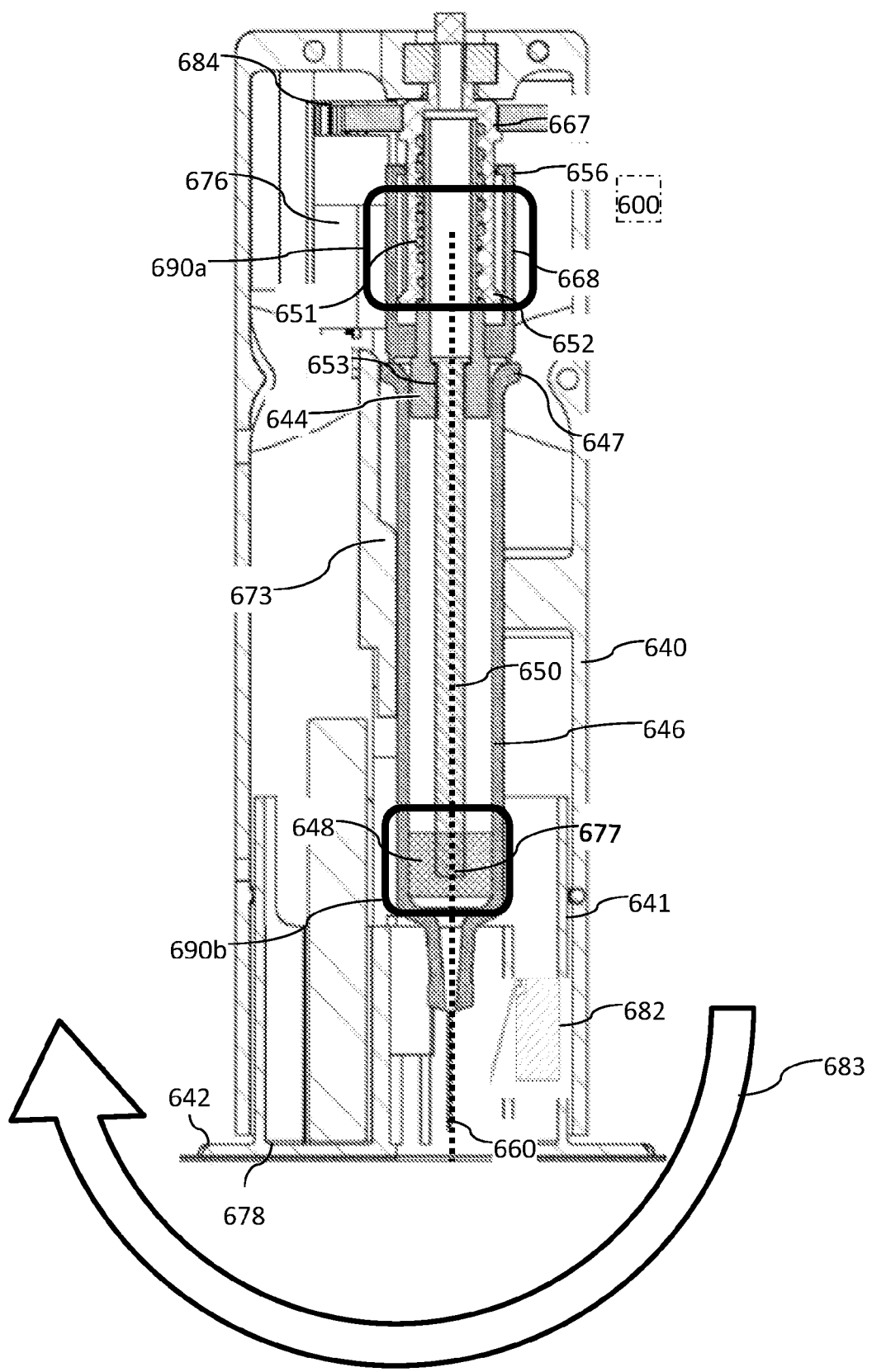

In some embodiments, once interference element 652 is overcome a course inner threading 655 in sleeve 667 rotates with respect to a course outer thread 651 of driver 644 drawing driver 644 and/or plunger 648 and/or syringe 646 and/or needle 660 proximally into a retracted state. For example, the course thread 651 has an opposite threading from the threading 653 between driver 644 and plunger rod 650. The same direction of rotation that drives plunger 648 distally before overcoming interference element 652 also draws back plunger 648 and/or syringe 646 and/or needle 660 proximally after overcoming interference element 652. Optionally needle 660 is retracted into a protected location inside housing 640 for example as illustrated in FIG. 6D. Alternatively or additionally, course thread 651 may have an the same direction of threading as threading 653 between driver 644 and plunger rod 650 and optionally rotation may be reversed to retract needle 660.

FIG. 6D is a schematic cross sectional side view illustrating injector 600 in a safe state after finishing injection. Needle 660 point has optionally been retracted into a protected location within housing 640. Syringe 646 has optionally been retracted. In exemplary injector 600, when syringe 646 is retracted, it no longer depresses switch 682. Switch 682 may be biased off and/or raising syringe 646 may shut off motor 676.

In some embodiments one or more windows may be supplied. A user may be able to determine a status of the device by viewing for the windows. For example in FIG. 6D, injector 600 has been supplied with two windows 690a,b. For example window 690a is located such that during injection, the user views inner sleeve 667 through window 690a. When outer sleeve 668 has been retracted, it may optionally slide over inner sleeve 667. After outer sleeve 668 has been retracted, the user views outer sleeve 668 through window 690a. Optionally window 690a may serve as an indicator whether it is safe to remove the injector. For example, outer sleeve 668 may be colored green and/or driver 644 and/or inner sleeve 667 may be colored red. For example, as long as the user sees red in window 690a needle 660 tip has not been retracted and/or it is unsafe to remove the injector from the patient's skin; and/or when the user views green through window 690a needle 660 has been retracted and/or discharge has ceased and/or it is safe to remove the injector from the skin of the patient. Optionally, window 690b may be used to indicate whether an entire payload of medicine has been administered. For example, syringe 646 may be made of a transparent material. For example, during injection, the user can see the medicine through window 690b; after syringe 646 is retracted if the payload has been fully discharged then the user will view plunger 648 through window 690b. Optionally, if the user sees plunger 648 through both window 690b and outer sleeve 668 through window 690a then the user can ascertain that it is safe to remove the injector and/or that the drug was fully discharged.

In injector 600, for example, after retraction of the needle the device may be twisted such that one side of the adhesive is lifted and/or peeled (as illustrated by arrow 683 in FIG. 6D) from the skin while the far edge of the base of the injector remains in contact with the skin and serves as a fulcrum.

Figure 6E:
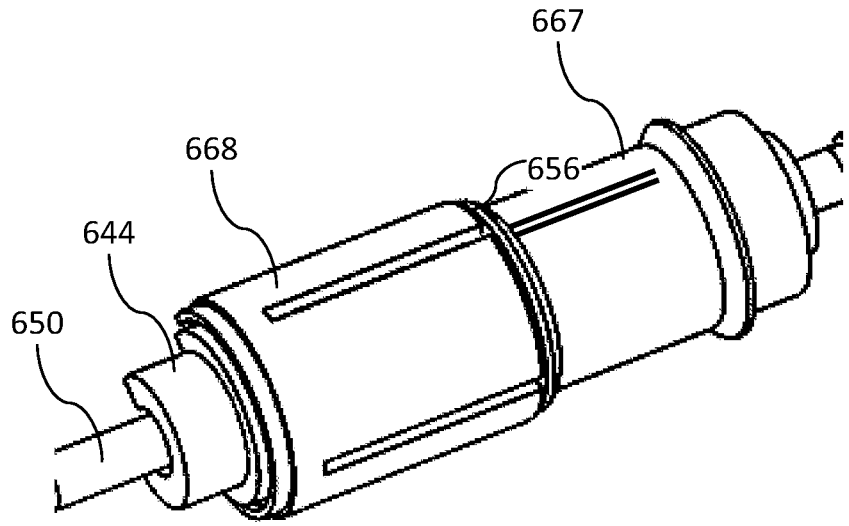
Figure 6F:
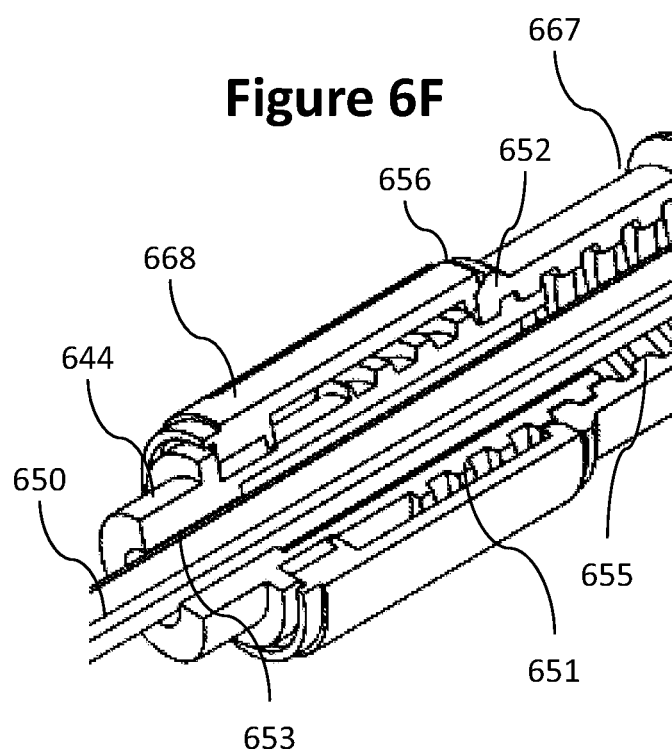

FIGS. 6E and 6F illustrate an external view and cut away view respectively of a needle retractor according to exemplary injector 600 of the current invention. Injector 600 may optionally be designed such that, under sufficient linear stress, support 656 of external sleeve 668 deforms and/or opens to pass over resistance element 652. Optionally, transmission 684 and/or inner sleeve 667 may be formed of one or more pieces of molded plastic. Optionally outer sleeve 668 and/or driver 644 may be formed of one or more pieces of molded plastic.

FIG. 6F, illustrates details of a rotary needle retractor according to an embodiment of the current invention. FIG. 6F illustrates driver 644 before needle retraction (for example in a secured state, an enabled state and/or an active state). In the exemplary embodiment, driver 644 is engaged by a set of fine screw threads 653 to rod 650. In the exemplary embodiment, driver 644 is engaged by a set of course screw threads 651, 655 to inner sleeve 667. Optionally, course screw threads 651, 655 are threaded in an opposite sense from fine screw threads 653.

In the exemplary embodiment, prior to needle retraction, sleeve 667, 668 and driver 644 are prevented from sliding longitudinally with respect one another. While sleeves 667, 668 and driver 644 are prevented from relative longitudinal movement, threads 651 and 655 prevent inner sleeve 667 and driver 644 from rotating with respect to one another.

In some embodiments, motor 676 drives transmission 684 to rotate inner sleeve 667. Optionally, before needle retraction, rotating inner sleeve 667 rotates driver 644. The sense of screw threads 653 and the rotating direction of motor 676 are optionally chosen such that rotating driver 644 relative to rod 650 pushes rod 650 and/or plunger 648 distally, optionally discharging a drug.

When plunger 648 has reached the distal end of syringe 646, rod 650 is prevent from further distal movement. Torque applied to driver 644 produces a strong proximal stress on driver 644 and/or outer sleeve 668. The strong proximal stress overcomes and/or releases interference element 652. Once interference element 652, is released outer sleeve 668 and/or driver 644 can move longitudinally with respect to inner sleeve 667. Further rotation of inner sleeve 667 rotates sleeve 667 with respect to driver 644. The sense of screw threads 655 and 651 and the rotating direction of motor 676 are optionally chosen such rotating driver 644 relative to sleeve 667 draws driver 644 and/or rod 650 and/or plunger 648 and/or syringe 646 and/or needle 660 proximally, optionally retracting needle 660. Optionally the pitch of screw threads 651, 653 and/or 655 can be tuned to achieve a desired rate of medicine discharge and/or needle retraction for a given rotation rate of the motor. In some embodiments, as rod 650 and/or plunger 648 are drawn proximally, friction between plunger 648 and syringe 646 draws syringe 646 and/or needle 660 proximally. Alternatively or additionally, outer sleeve 668 may be attached to syringe 646. Drawing back on driver 644 may draw outer sleeve 668 and syringe 646 back with it. In some embodiments additional threaded elements may be added to produce a multi-part telescoping assembly for extending plunger 648 to discharge medicine and/or for retracting needle 660. In some embodiments some or all of rod 650, inner sleeve 667, and/or outer sleeve 668 and/or transmission 684 may be formed of molded plastic and or other materials.

7 Stabilized Pen Injector

FIGS. 7A-H illustrate a stabilized injector 700 according to some embodiments of the present invention. Exemplary injector 700 is an automated injection device in some ways similar to a pen injector. Optionally injector 700 may be loaded with a standard type syringe 646 and/or hypodermic needle 660. Optionally syringe 646 may be supplied loaded with medicine and/or covered with a sterile needle cover 791. Syringe 646 may be loaded into injector 700 with in a sterile state with needle cover 791 in place. Injector 700 may include for example an adhesive 678 base 642. In some embodiments, adhesive 678 base 642 may assist a user to hold injector 700 steady on the skin of a patient for an extended period. For example, injector 700 may be used to give injections of volume ranging between 0.5 and 3.0 ml over a time period ranging between 30 sec to 180 sec.

Figure 7A:
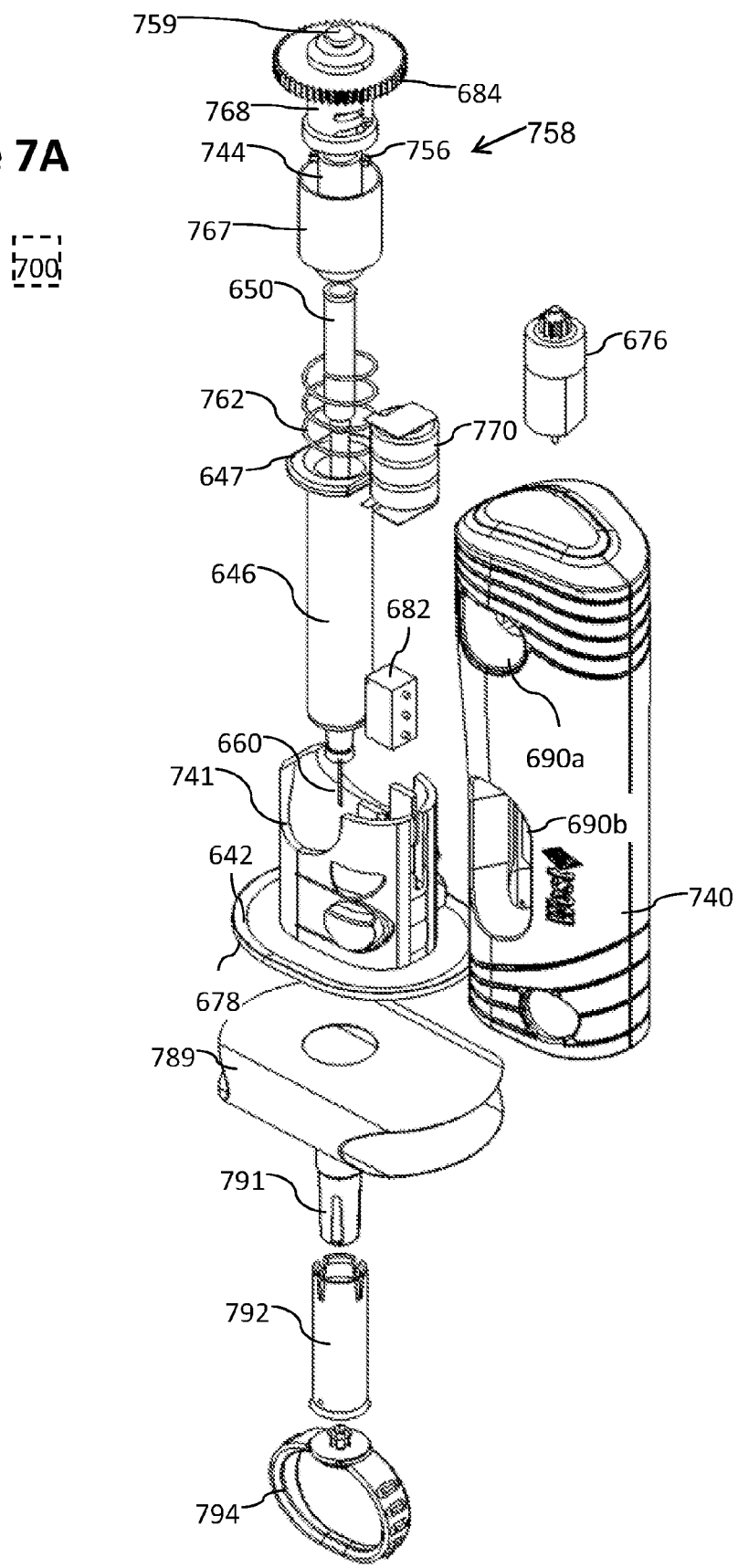

FIG. 7A illustrates an exploded view of injector 700. Some components of the exemplary embodiment of injector 700 which are similar to corresponding parts of the exemplary embodiment of injector 600 are marked with the same number as the corresponding parts of the exemplary embodiment of injector 600.

In the exemplary embodiment of injector 700 a power supply (for example batteries 770) may optionally supply power to gear motor 676. FIGS. 7A,B illustrate flange 647 of syringe 646. Optionally flange 647 has at least one non-rounded edge which may be held inside an autoinjector (for example autoinjectors 400, 600 and/or 700) preventing rotation of syringe 646. Outer housing 740 and/or shield 741 of injector 700 are similar to outer shell 640 and/or shield 641 of injector 600.

Some embodiments of a stabilized autoinjector (for example as illustrated in injector 700 but optionally included in injectors 600 and/or embodiments 400 and/or 200 and/or 100) may include a safety cover and/or an adhesive protector and/or a handle. Details of an exemplary embodiment of safety cover 792, adhesive protector 789 and handle 794 are illustrated in FIGS. 7C-H.

Figure 7B:
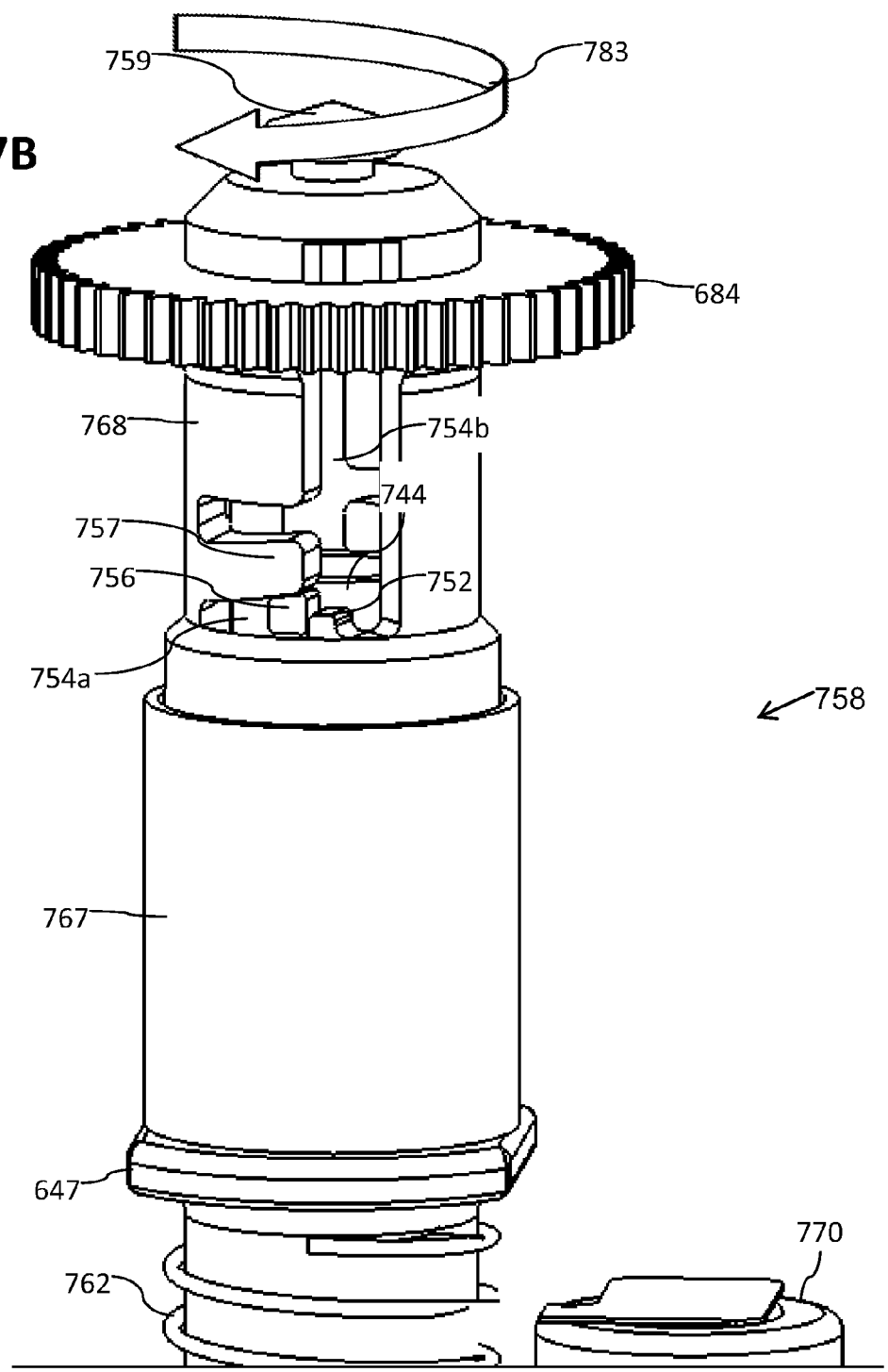

FIG. 7B illustrates exemplary retraction mechanism 758. Retraction mechanism 758 is optionally activated by a combination of torque and linear stress. For example retraction mechanism 758 is optionally activated may when plunger 648 is blocked for example when it reaches the end of injection (for example as described in regards to FIGS. 6A-D and/or due to an occlusion of needle 660).

In some embodiments, during drug discharge a motor (for example motor 676) rotates transmission 684 in the direction of arrow 783. Transmission 684 may optionally be rigidly connected to and/or integrally molded with inner sleeve 768. Rotating transmission 684 may also rotate inner sleeve 768. A pin 756 protrudes from driver 744 into a nearly lateral slot 754a in sleeve 768. While pin 756 is in slot 754a, driver 744 is prevented from moving longitudinally with respect to inner sleeve 768. In some embodiments syringe 646 is supported (from moving proximally) by driver 744.

In some embodiments, when there is a strong linear force on driver 744 in the proximal direction and/or there is a strong torque on sleeve 768 in the direction of arrow 783, arm 757 is deflected upward and pin 756 slides past an interference element 752 into a longitudinal slot 754b. In slot 754b pin 756 may slide longitudinally (in the proximal direction). A geometry of pin 756 and/or interference element 752 may be chosen to achieve a desired resistance to movement. For example, pin 756 and/or interference element 752 may have a squared side, a flat side, a rounded side etc.

In some embodiments, a spring (for example spring 762) biases syringe 646 in the proximal direction. For example spring 762 may apply a proximal force to flange 647. Optionally another biasing element may be used in place of spring 762. For example, a biasing element may include a stretched element (for example a rubber band and/or a twisted elements and/or a deflected plastic element).

Optionally when pin 756 enters longitudinal slot 754b, spring 762 pushes syringe 646 and/or outer sleeve 767 and/or needle 660 and/or driver 744 and/or pin 756 proximally, retracting needle 660. Optionally, needle 660 may be held in the retracted position by spring 762. Alternatively or additionally a locking mechanism may be included to lock needle 660 in the retracted position, for example, a one way catch and/or an interference element may lock against syringe 646 as it is retracted and/or against pin 756 in slot 754b. Optionally, in injector 700 driver 744 includes two molded plastic telescoping pieces. One piece is optionally integrally molded with outer sleeve 767. Optionally, sleeve 767 and/or driver 744 may be made as a single piece and/or multiple parts. They may be formed of plastic and/or another material and/or they may be molded and/or formed by another process.

Figure 7C:
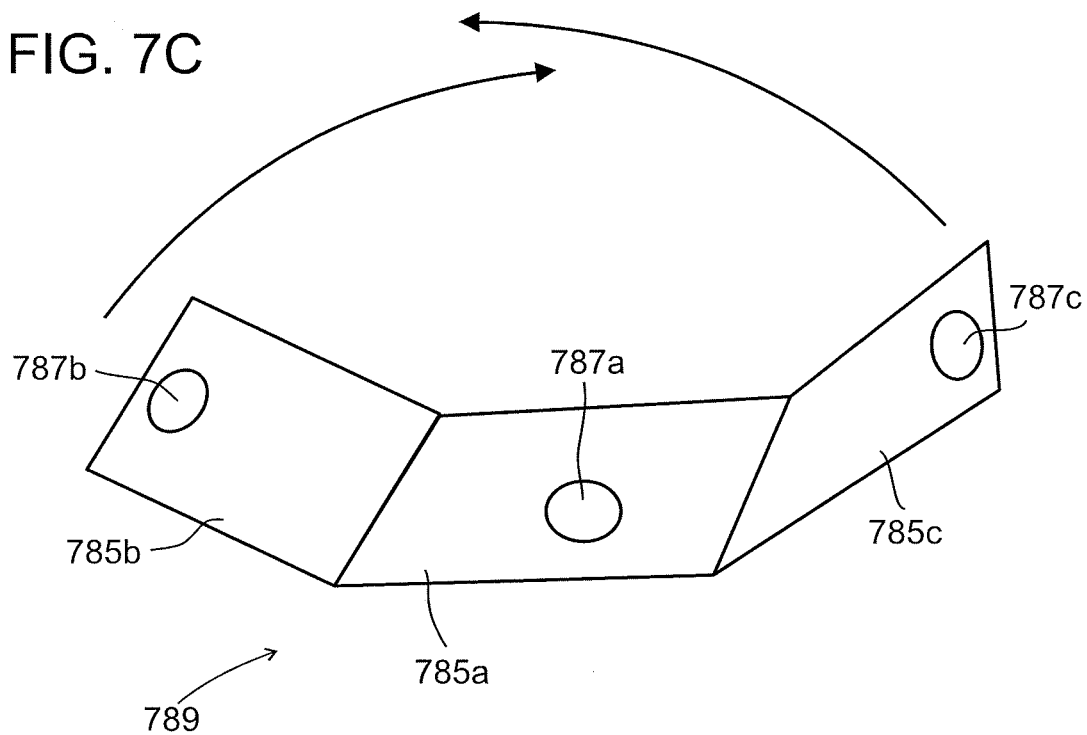
Figure 7D:
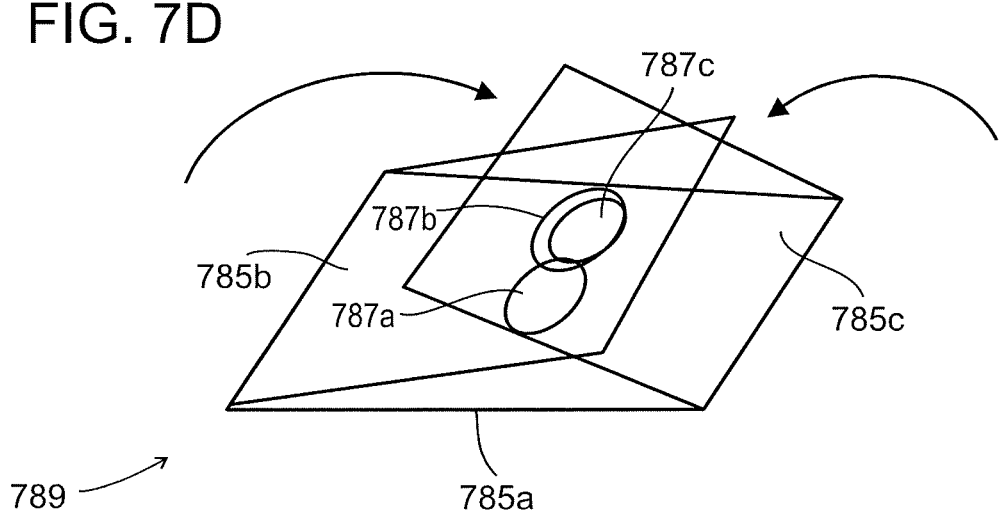

FIGS. 7C and 7D illustrate an exemplary method of folding adhesive protector 789. For example, adhesive protector may include three folded portions 785a, 785b, and 785c. For example, adhesive protector may include three holes 787a, 787b, and 787c. When folded, the side portions 785b,c may fold over the center portion 785a. Side holes 787c,b may line up with center hole 787a. Alternatively or additionally, an adhesive protector may have only one fold and/or one side portion and/or peeling may be from one side only.

In some embodiments, portion 785a will be adhered to base 642 with the needle opening accessible through holes 787a-c. A safety cover (for example cover 792) may protrude through holes 787a-c. The safety cover may optionally be connected to portions 785b,c. The safety cover may pass freely through hole 787a and/or not be connected to portion 785a of adhesive protector 789.

FIGS. 7E-H illustrate removal of an exemplary safety cover 792, needle cover 791 and/or adhesive protector 789. For example, while safety cover 792 is mounted to needle cover 791, safety cover may prevent deployment and/or activation of the injector. For example, safety cover 792 and handle 794 may supply a convenient means of removing needle cover 791 and/or adhesive protector 789.

FIG. 7E illustrates injector 700 in a safe state for storage and/or transport. Needle cover 791, safety cover 792 and adhesive protector 789 are in place. Adhesive protector 789 is folded for example as illustrated in FIGS. 7C,D. Needle cover 791 (not seen in the drawing) may optionally preserve the sterility of needle 660. Safety cover 792 surrounds and grasps needle cover 791. Safety cover 792 may prevent inadvertent activation of the injector and/or protect users from a needle stick hazard.

FIG. 7F illustrates the beginning of removal of safety cover 792. A user pulls handle 794 away from needle 660. Handle 794 pulls needle cover 791 out the needle hole of injector 700 and through hole 787a. As cover 792 is pulled away from base 642, portions 785b,c of adhesive protector unfold while portion 785a remains adhered to base 642.

FIG. 7G illustrates that as safety cover is pulled further away from base 742 portions 785b,c of adhesive protector 789 pull and peel portion 785a away from base 742.

FIG. 7H illustrates cover 792 and protector 789 fully removed from injector 700, such that injector 700 is enabled and/or ready to adhere to a patient and/or ready for activation.

Figure 7I:
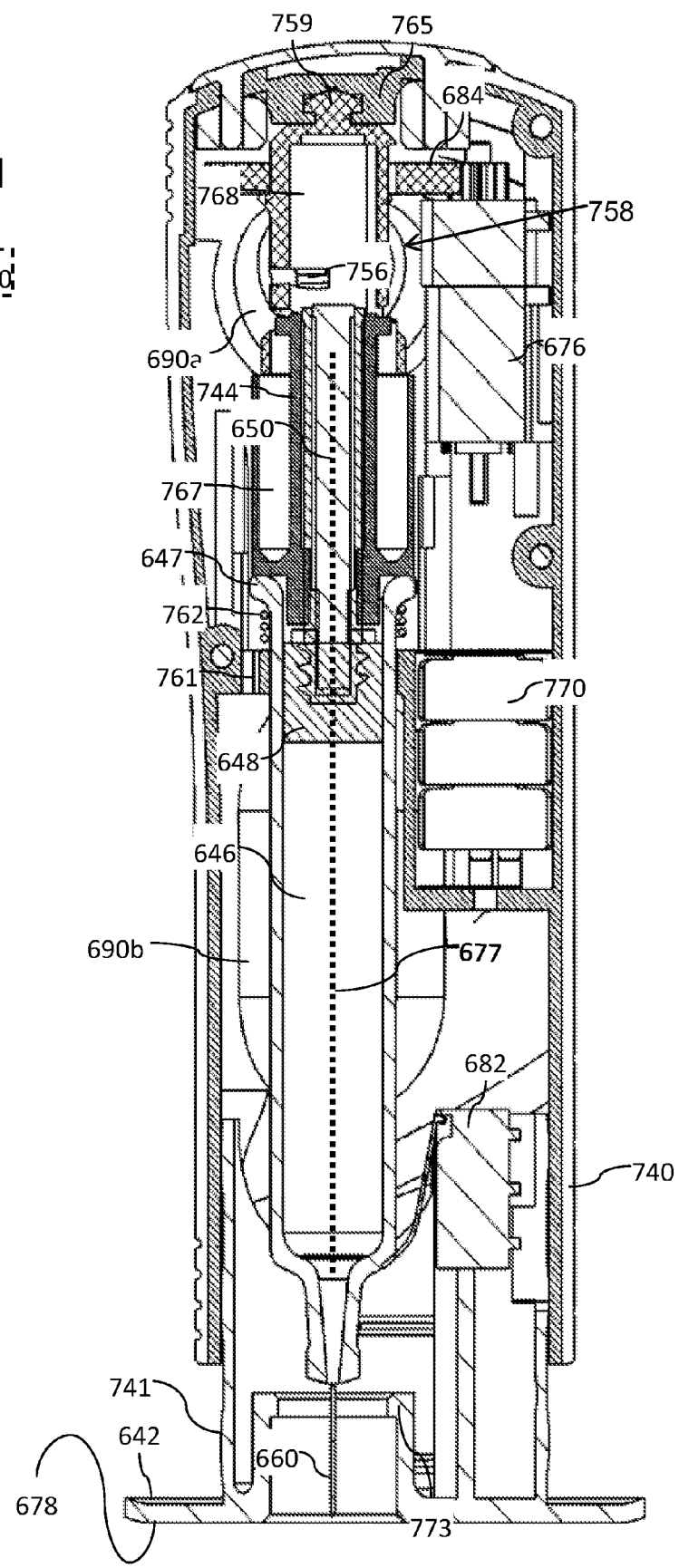

FIG. 7I illustrates exemplary embodiment 71 assembled and/or in an enabled state before insertion of needle 660 into a patient. FIG. 7I illustrates various optional details and/or supporting structures for syringe 646 and/or plunger.

In injector 700, syringe 646 is held to outer housing 740 by a socket 761. Socket 761 allows syringe 646 to slide axially with respect to housing 740 but not to move laterally. In injector 700, transmission 684 is held rotatably fixed to housing 740 by bearing 759 in a hub 765.

Figure 7J:
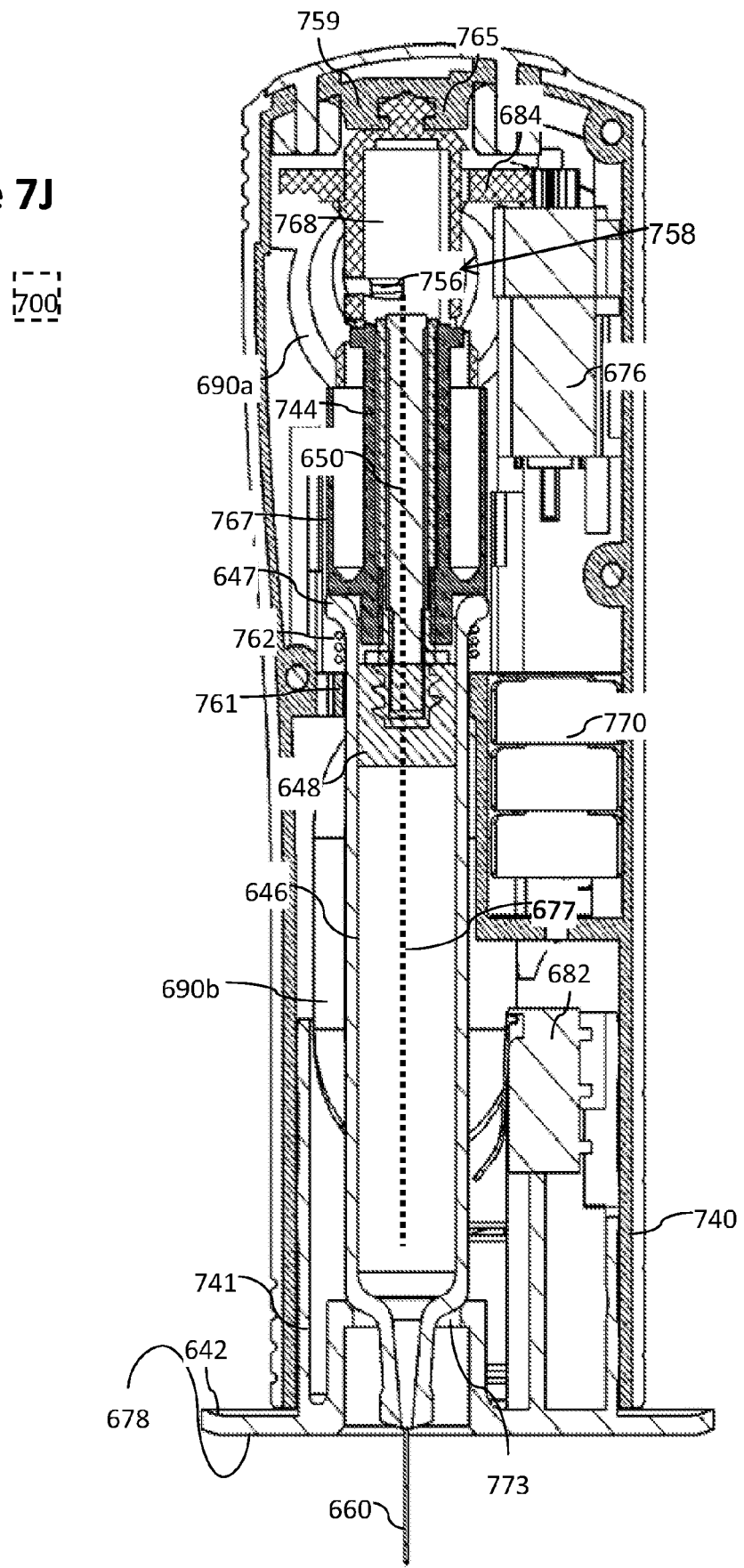

FIG. 7J illustrates exemplary injector 700 in an active state. For example when the injector is in the enabled state, a user may place adhesive against the skin of a patient and push downward (distally) on housing 740. Housing 740 and its contents (for example syringe 646, transmission 684, locking assembly 758 etc.) along with needle 660 are all pushed distally along the axis of needle 660. As needle 660 moves distally, the needle tip passes through a hole in shield 741. For example, in operation, needle 660 may protrude from injector 600 into a patient. Optionally, in operation, needle 660 may be in fluid communication with syringe 646 and/or the patient. For example needle 660 may supply a fluid pathway for discharging medicine directly from syringe 646 through needle 660 into the patient.

In some embodiments, when needle 660 is in the extended position, the front end of syringe 646 seats into a bracket 773. Bracket 773 may optionally hold syringe 646 steady and/or prevents further longitudinal movement and/or prevent lateral movement with respect to housing 740.

Figure 7K:
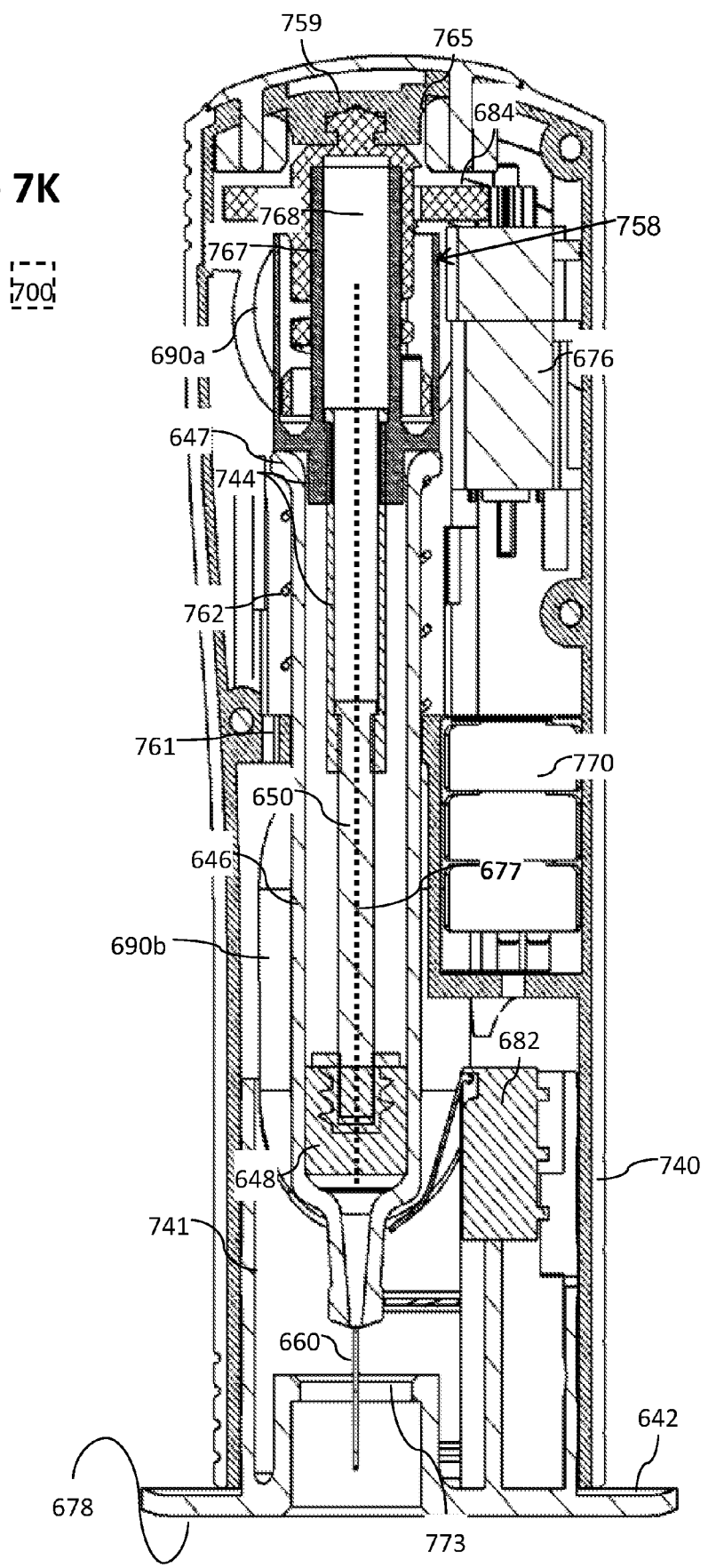

FIG. 7K illustrates injector 700 after needle retraction. Optionally driver 644 includes a telescopic assembly, which is shown in an extended state in FIG. 7K. Optionally, after retraction of needle 660, the entire device may be twisted to peel adhesive 678 from the skin.

Various aspects or features illustrated herein with respect to a particular embodiment may be combined with other embodiments. For example, needle 460 and 560 of embodiment 400 and 500 are shown mounted at an angle to base 442 or 542. Alternatively or additionally they may be perpendicular to the base. For example, needles 660 of embodiments 600 and 700 are shown perpendicular to base 642. Alternatively or additionally they may be at an angle to the base. Needle covers and/or protective covers illustrated in one embodiment may be used with another embodiment. Retraction mechanisms illustrated in one embodiment may be used with another embodiment. A clip, an interference element, a catch and/or another locking mechanism may hold an injector in one or another state. For example an interference element may hold a needle in a retracted position and/or in the extended position.

Figure 8:
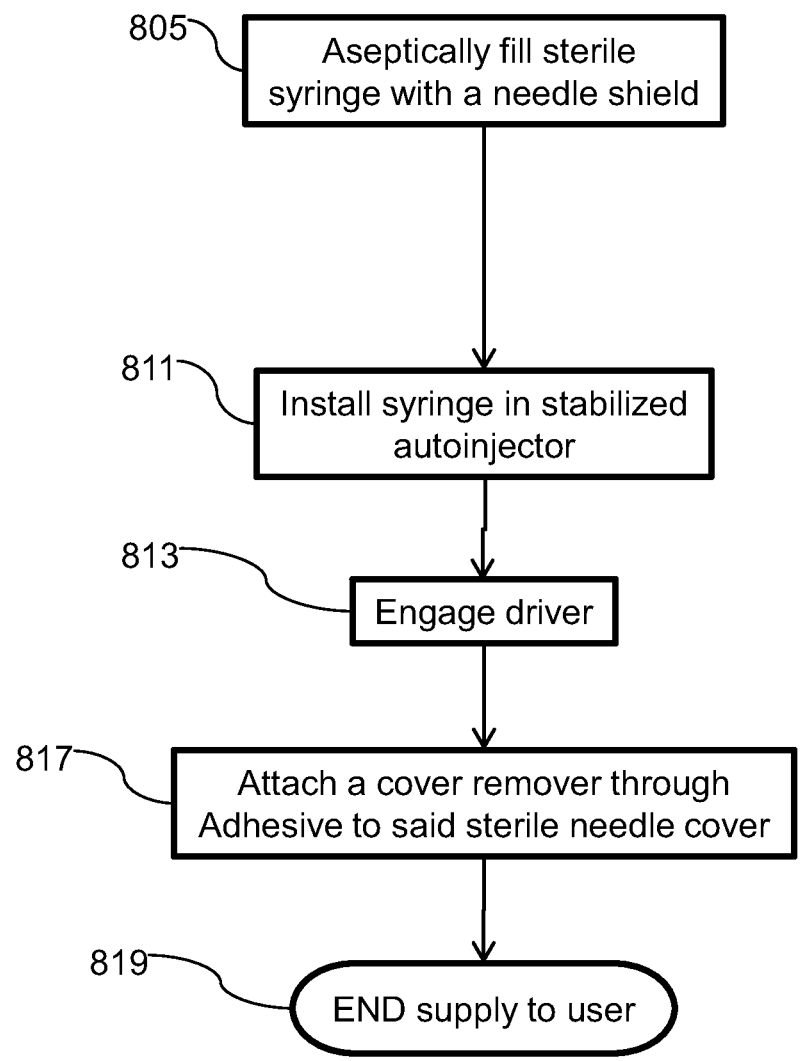
FIG. 8 is a flow chart illustration of a method of manufacture of a stabilized pen injector according to an embodiment of the present invention.

FIG. 8 is a flow chart illustration of a method of manufacture of a stabilized pen injector according to an embodiment of the present invention. In the method a preloaded sterile syringe and needle may optionally be installed into an autoinjector for direct injection into a patient. For example the method of manufacture illustrated in FIG. 8 may optionally be used in manufacturing one, some and/or any of the embodiments of an injector illustrated herein above and/or below.

In some embodiments a syringe is preloaded 805 with a medicine. For example the volume of preloading medicine may range between 0.5 and 1 ml and/or between 1 and 5 ml and/or greater than 5 ml of medicine. Preloading 805 may optionally be performed on standard syringe equipment and using standard filling procedures. Optionally the syringe may be a standard type syringe. For example preloading may be done in an aseptic environment. Optionally, a sterile needle and/or needle cover may be attached before filling the syringe. For example, the syringe may be filled while attached to a sterile needle and/or a sterile needle cover. Alternatively or additionally, the syringe may be attached to a sterile needle and/or a sterile needle cover while being filled and/or after being filled. Sterility of the needle may optionally be protected by a needle cover (for example cover 791).

In some embodiments, the preloaded syringe with the sterile, protected needle may be installed 811 in an autoinjector including an adhesive stabilizer (for example one of the autoinjectors described herein above). Optionally, installing 811 the syringe may include engaging 813 a driver to a power source, for example a battery (for example directly and/or via a motor and/or transmission) and/or a mechanical power source for example a spring.

In some embodiments, the fluid path of the injector may include the medicine container and/or the needle. For example, in operation, medicine stored in the container may pass directly from the container to the needle and/or from the needle directly to the patient. Optionally, the entire fluid path may be in a complete and/or sterile and/or assembled and/or protected state prior to and/or during filling of the container. For example, a syringe medicine container and/or needle may be filled and sealed under aseptic and/or sterile conditions, for example in an aseptic room. For example the syringe may be sealed by a needle cover and/or a plunger. Optionally, the syringe, with the fluid path in a sealed and/or protected state may be taken from the aseptic filling room and installed into an injector. Optionally, the fluid path may not require sterilization after being removed from the filling room and/or after installation into the injector.

In some embodiments, a cover remover (for example safety cover 792) may be attached 817 to the needle cover through a hole in the adhesive. In some embodiments, the hole in the adhesive may be surrounded by the adhesive. Alternatively or additionally, the hole may be surrounded by the adhesive on two sides and/or on three sides. For example, the adhesive may be made of two pieces, one piece on one side of the hole and another piece on another side of the hole. The autoinjector may then be ready to be supplied 819 to a user. For example the user may use the cover remover to remove the needle cover and/or to enable the injector.

Figure 9:
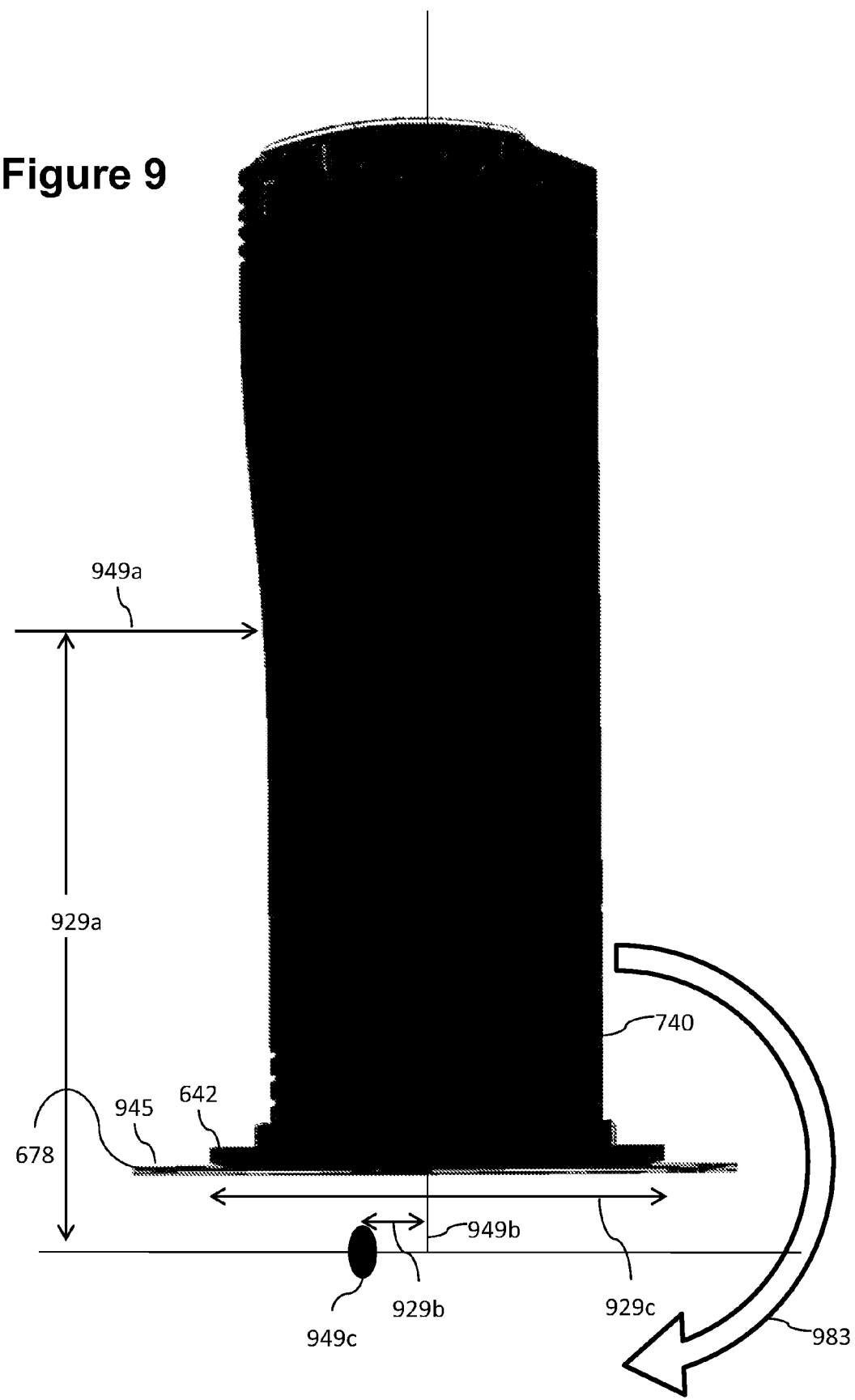
FIG. 9 illustrates an external view of a stabilized injector according to an embodiment of the current invention.

FIG. 9 illustrates an external view of a stabilized injector according to an embodiment of the current invention. In FIG. 9 exemplary dimensions are shown to help understand the relationship between the size and weight of the injector and the strength and geometry of the adhesive. For example, any, some and/or all of the features and/or dimensions described herein below may apply to any, some and/or all of the embodiments described herein above.

In some embodiments, the height of an autoinjector (perpendicular to the adhesive layer) may be greater than then width of the adhesive layer (for example the height may be greater than the greatest length between any two points on the adhesive layer). For example, the distance 929$a$ from the longitudinal center of mass 949$a$ of the injector and the adhesive surface 678 may range for example between 50±10 mm and/or the longitudinal center of mass may range for example between 60 and 80 mm from the adhesive. In some embodiments, the longitudinal center of mass may be greater than for example between 80 mm from the adhesive. The distance 929$b$ between the lateral center of mass 949$b$ of the injector and the center of adhesion 949$c$ on the base of the apparatus (when the weighted center of force on the adhesive when the injector is twisted off the skin in the direction of the arrow 983 in FIG. 9) may range, for example between 12.5±4 mm. The width 929$c$ of base 642 may range, for example, between 60±15 mm. There may optionally be a semi-stiff skirt 945 extending beyond the edge of base 642 for example between 0 to 2 mm and/or embodiments skirt 945 may extend for example between 4 to 10 mm beyond base 642. In some embodiments, the width of skirt 945 may vary at various points around base 645. (For example the skirt may be made of plastic, for example Polyethylene terephthalate (PET) and/or Polycarbonate and/or ABS. The thickness may range for example between 0.1 to 0.8 mm.). The thickness of adhesive layer 678 may range between 0.1 and 1 mm. An injector may weigh for example 50±20 g. Then the resting torque adhesive when the injector is adhered to a vertical object will be approximately 50 mm×50 g=2500 g×mm. The strength of adhesion necessary to hold the injector to the patient will be approximately 2500 g×mm/12.5 mm=200 g. In some embodiments, movements of the user may place a considerably stress on the injector than the static stress. For example an adhesive may be provided to give a total adhesive strength ranging between 500 to 1500 g.

In some embodiments, the adhesive will be less strong and/or maybe easier to remove. For example the strength of the adhesive may be less than 500 g (for example the user may have to hold the injector with his hand to prevent it from falling, especially when the user is moving). Alternatively or additionally the adhesive may not include semi-stiff skirt 945.

In some embodiments, the adhesive may include a semi stiff skirt. The skirt may make the injector more stable. Alternatively or additionally, the adhesive may be connected to a stiff base (for example the base of the injector) without a semi-stiff skirt. For example, an embodiment without a semi stiff skirt may be easier to remove after the end of injection.

It is expected that during the life of a patent maturing from this application many relevant technologies will be developed and the scope of the terms are intended to include all such new technologies a priori.

As used herein the term "about" refers to ±5%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An autoinjector comprising:
   a drug container having a principle longitudinal axis;
   an adhesive layer which in operation is in contact with a skin of a patient in a vicinity of an injection site and which in operation is attached to said drug container orienting said principle longitudinal axis at an angle between 60 to 120 degrees to said injection site; and
   a driver for discharging a contents of said drug container into said patient;
   wherein in operation, said drug container moves with respect to said adhesive layer in a direction parallel to said principle longitudinal axis.

2. The autoinjector of claim 1 further including:
   a needle in fluid communication with said drug container, said needle rigidly connected to said drug container and wherein in operation at least of portion of said needle projects from the autoinjector into said patient.

3. The autoinjector of claim 2, wherein said needle includes a straight needle and said needle protrudes from said drug container in a direction substantially parallel to said principle longitudinal axis.

4. The autoinjector of claim 2, wherein in operation said needle forms a fluid path directly from said drug container into said patient.

5. The autoinjector of claim 1, wherein said driver is internally powered.

6. The autoinjector of claim 5, further comprising:
   a motor for powering said driver.

7. The autoinjector of claim 1, wherein said driver is configured for discharging said drug over a time period ranging between 30 seconds and 180 seconds.

8. The autoinjector of claim 1, wherein a volume of said drug container is between 0.5 and 3 ml.

9. The autoinjector of claim 8, wherein said automatic safeguard mechanism includes a needle retractor.

10. The autoinjector of claim 9, wherein the needle retractor is a rotary needle retractor.

11. The autoinjector of claim 1, further comprising:
    a hypodermic needle and wherein said discharging is through said hypodermic needle; and
    an automatic safeguard mechanism protecting said hypodermic needle at a completion of said discharging.

12. A method of injecting a substance into a patient comprising:
    fastening an injector to the patient;
    moving a medicine container linearly with respect to said injector to insert into the patient a needle rigidly attached to said medicine container; and
    discharging the substance from said medicine container through said needle into the patient while said injector remains fastened to the patient.

13. The method of claim 12, wherein said discharging is a continuous dose of between 0.5 and 3 ml.

14. The method of claim 12, wherein said discharging continues for between 20 and 180 sec.

15. The method of claim 12, wherein said fastening includes adhering an adhesive to the patient.

16. The method of claim 12, wherein said moving is parallel to a principle longitudinal axis of said medicine container.

17. The method of claim 12, wherein said discharging is self powered.

18. The method of claim 17, wherein said discharging is powered by a motor.

19. The method of claim 12, wherein said moving is in a direction at an angle of between 60 and 120 degrees of a surface of a skin of the patient at an injection site.

20. A method of manufacture of a stabilized autoinjector comprising:
    installing a syringe rigidly attached to a sterile needle and needle cap into a pen injector having an adhesive stabilizer; and
    attaching a cover remover to said needle cap through a hole in said adhesive stabilizer.

21. The method of claim 20, wherein said installing includes engaging a plunger of said syringe to a power supply.

22. The method of claim 20, further comprising:
    filling said syringe with between 1 and 3 ml of a medicine.

* * * * *